United States Patent
Gerson

(10) Patent No.: US 10,725,042 B2
(45) Date of Patent: Jul. 28, 2020

(54) METHODS OF DIAGNOSING AND TREATING CANCER

(71) Applicant: Case Western Reserve University, Cleveland, OH (US)

(72) Inventor: Stanton Gerson, Hunting Valley, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 845 days.

(21) Appl. No.: 13/900,166

(22) Filed: May 22, 2013

(65) Prior Publication Data

US 2014/0066464 A1     Mar. 6, 2014

Related U.S. Application Data

(60) Provisional application No. 61/650,305, filed on May 22, 2012.

(51) Int. Cl.

| | | |
|---|---|---|
| *A61K 31/519* | (2006.01) | |
| *A61K 31/131* | (2006.01) | |
| *G01N 33/573* | (2006.01) | |
| *A61P 35/00* | (2006.01) | |
| *A61K 31/513* | (2006.01) | |
| *A61K 31/7076* | (2006.01) | |
| *A61K 45/06* | (2006.01) | |
| *G01N 33/574* | (2006.01) | |
| *A61K 31/517* | (2006.01) | |
| *A61K 31/7072* | (2006.01) | |

(52) U.S. Cl.
CPC ......... *G01N 33/573* (2013.01); *A61K 31/131* (2013.01); *A61K 31/513* (2013.01); *A61K 31/517* (2013.01); *A61K 31/519* (2013.01); *A61K 31/7072* (2013.01); *A61K 31/7076* (2013.01); *A61K 45/06* (2013.01); *A61P 35/00* (2018.01); *C12Y 302/02027* (2013.01); *G01N 33/574* (2013.01); *G01N 2333/926* (2013.01); *G01N 2800/52* (2013.01)

(58) Field of Classification Search
CPC .. A61K 31/519; A61K 31/131; G01N 33/573; C12Y 302/02027; A61P 35/00
See application file for complete search history.

(56) References Cited

U.S. PATENT DOCUMENTS

2008/0234298 A1*    9/2008    Theuer et al. ............. 514/265.1

OTHER PUBLICATIONS

Weeks et al 'Mice deficient in uracil DNA glycosylase display increased sensitivity to the antifolate pemetrexed' Cancer Research, 71 (8 Supplement), Abstract 5490, Apr. 2011.*
Bulgar et al. "Removal of uracil by uracil DNA glycosylase limits pemetrexed cytotoxicity: overriding the limit with methoxyamine to inhibit base excision repair." Cell death & disease vol. 3,1 e252. Jan. 12, 2012. (Year: 2012).*

* cited by examiner

*Primary Examiner* — Theodore R. West
(74) *Attorney, Agent, or Firm* — Tarolli, Sundheim, Covell & Tummino LLP

(57) ABSTRACT

A method of determining the susceptibility of a cancer in a subject to treatment with an antimetabolite includes obtaining a sample of cancer cells from the subject, measuring the level of UDG expression in the cancer cells, and comparing the measured levels of UDG expression in the cancer cells to a control level.

13 Claims, 8 Drawing Sheets

Specification includes a Sequence Listing.

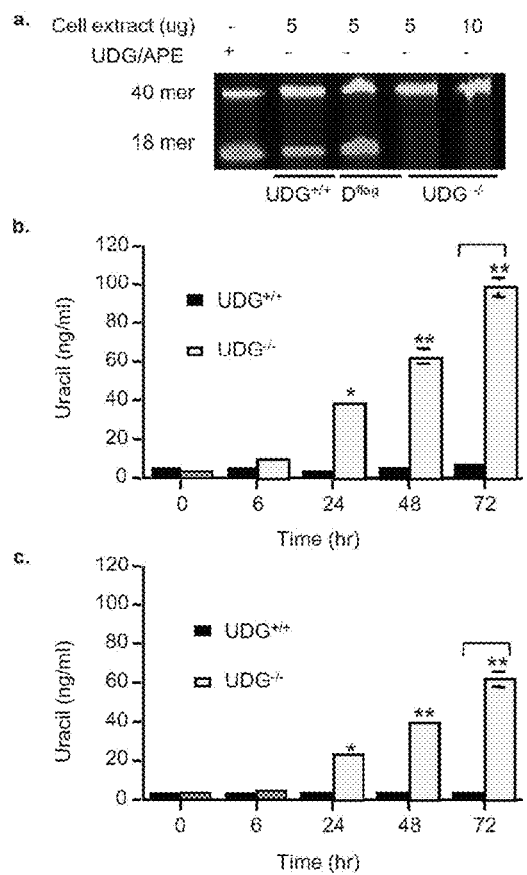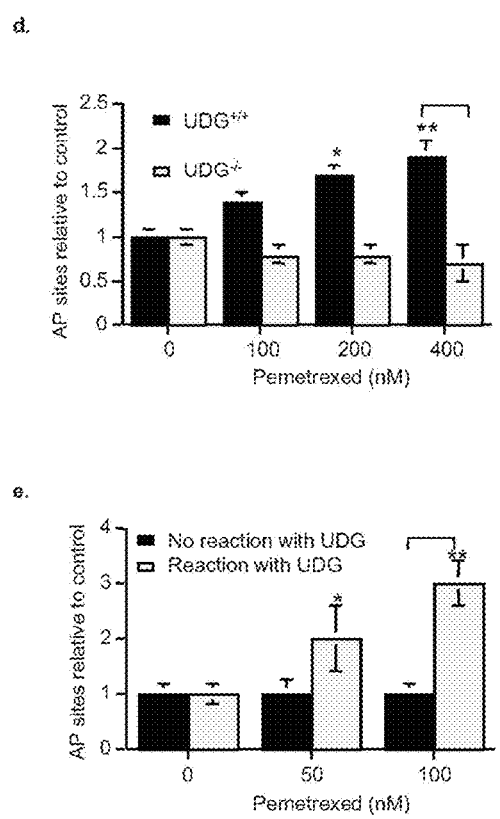
Figs. 1A-E

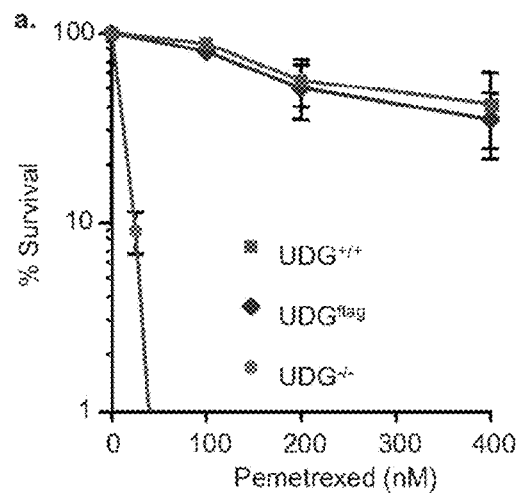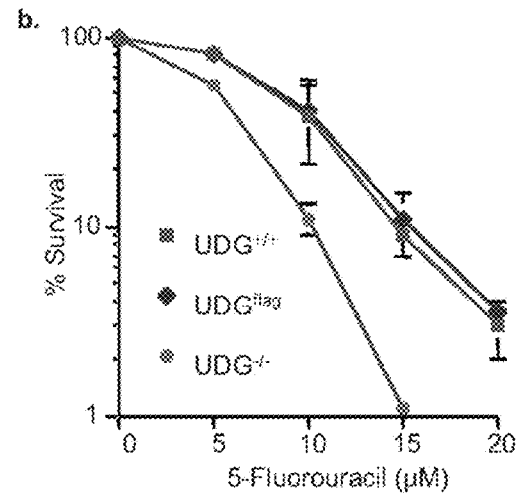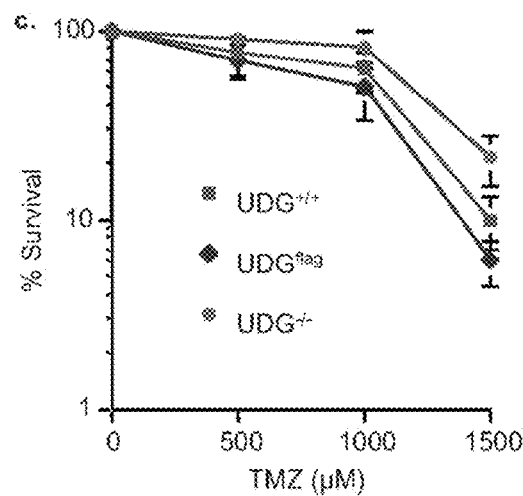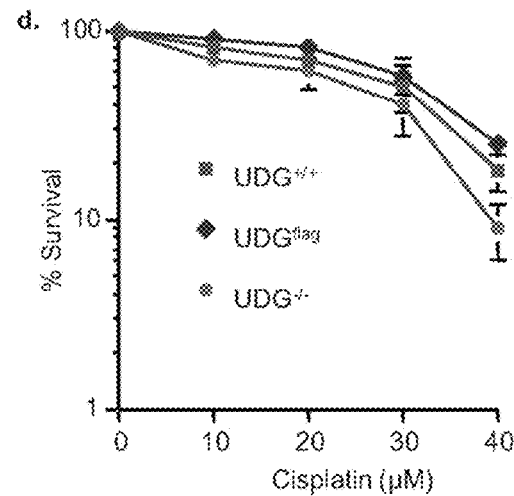
Figs. 2A-D

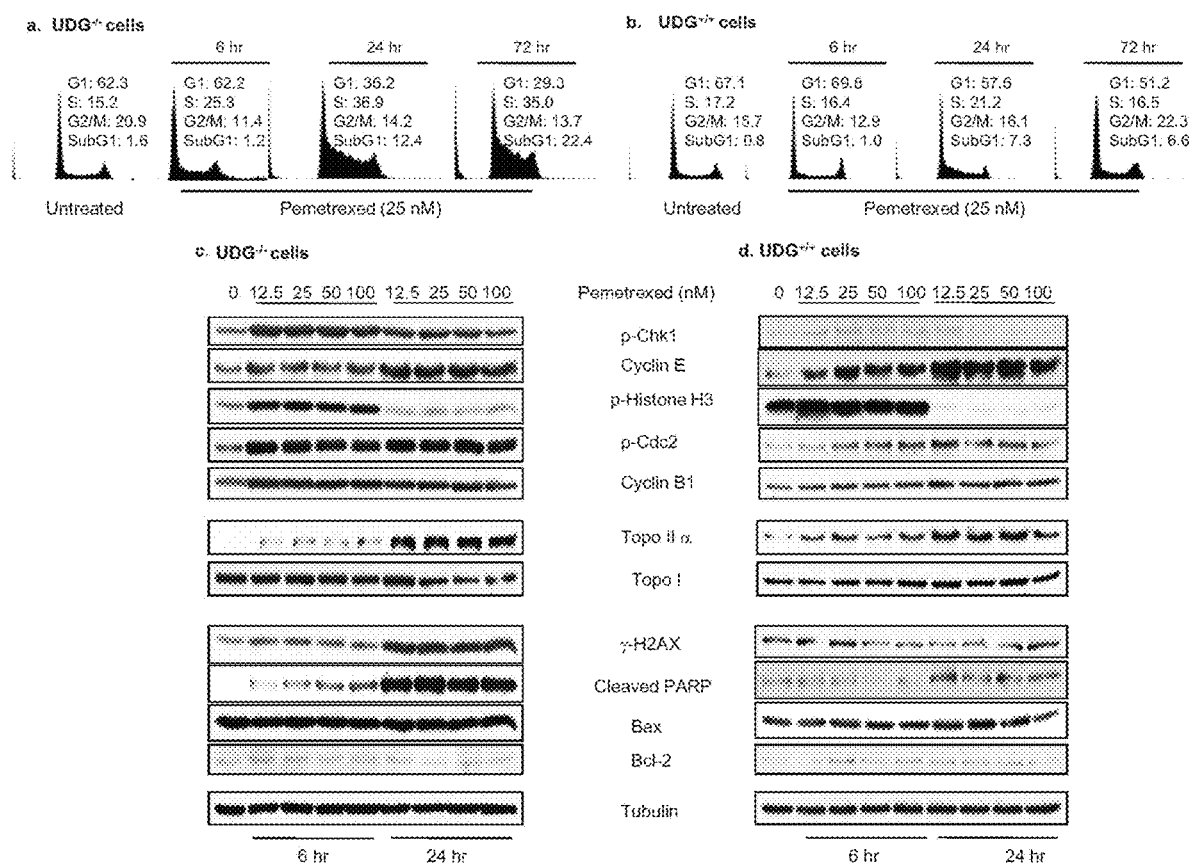
Figs. 3A-D

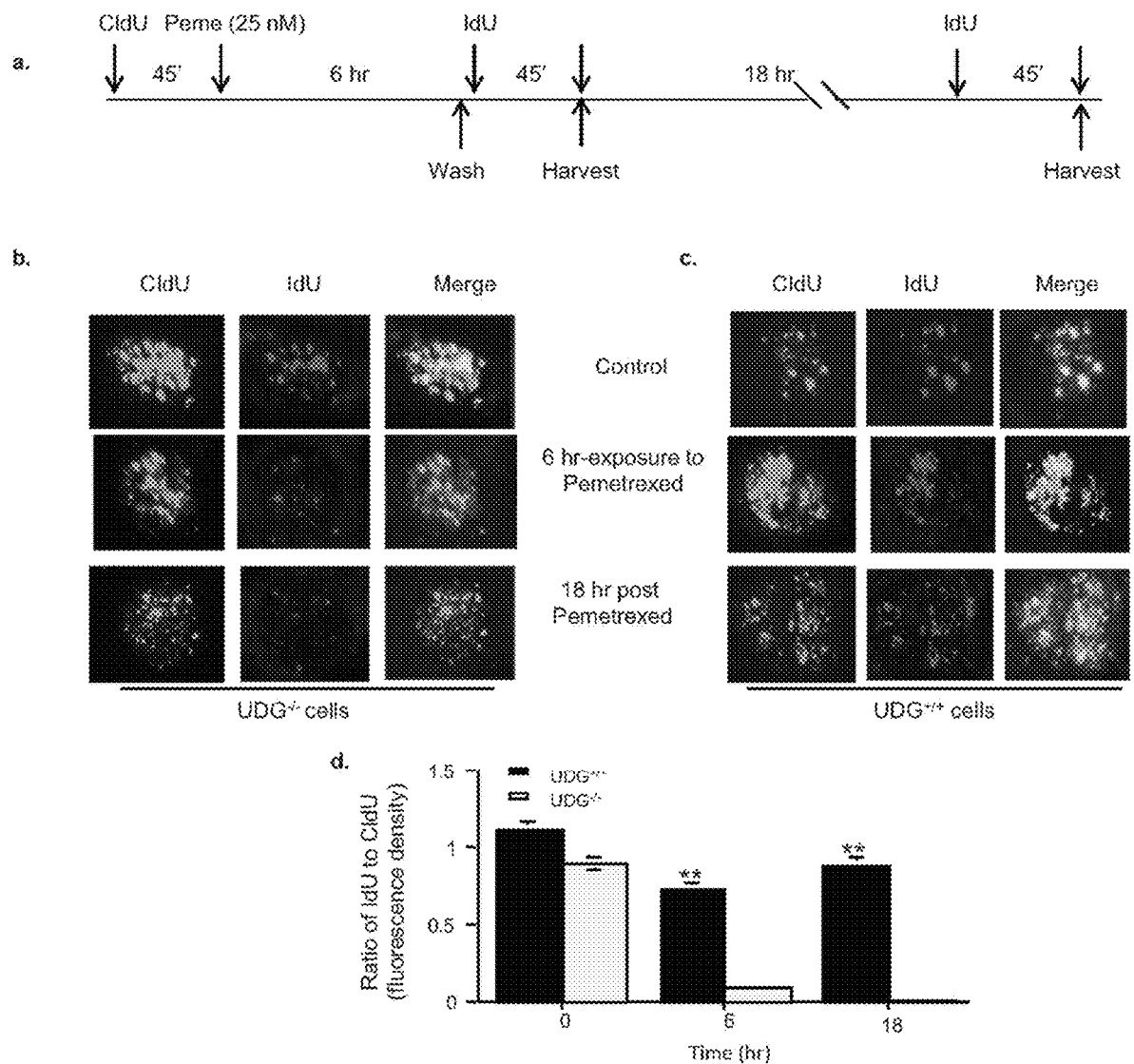
Figs. 4A-D

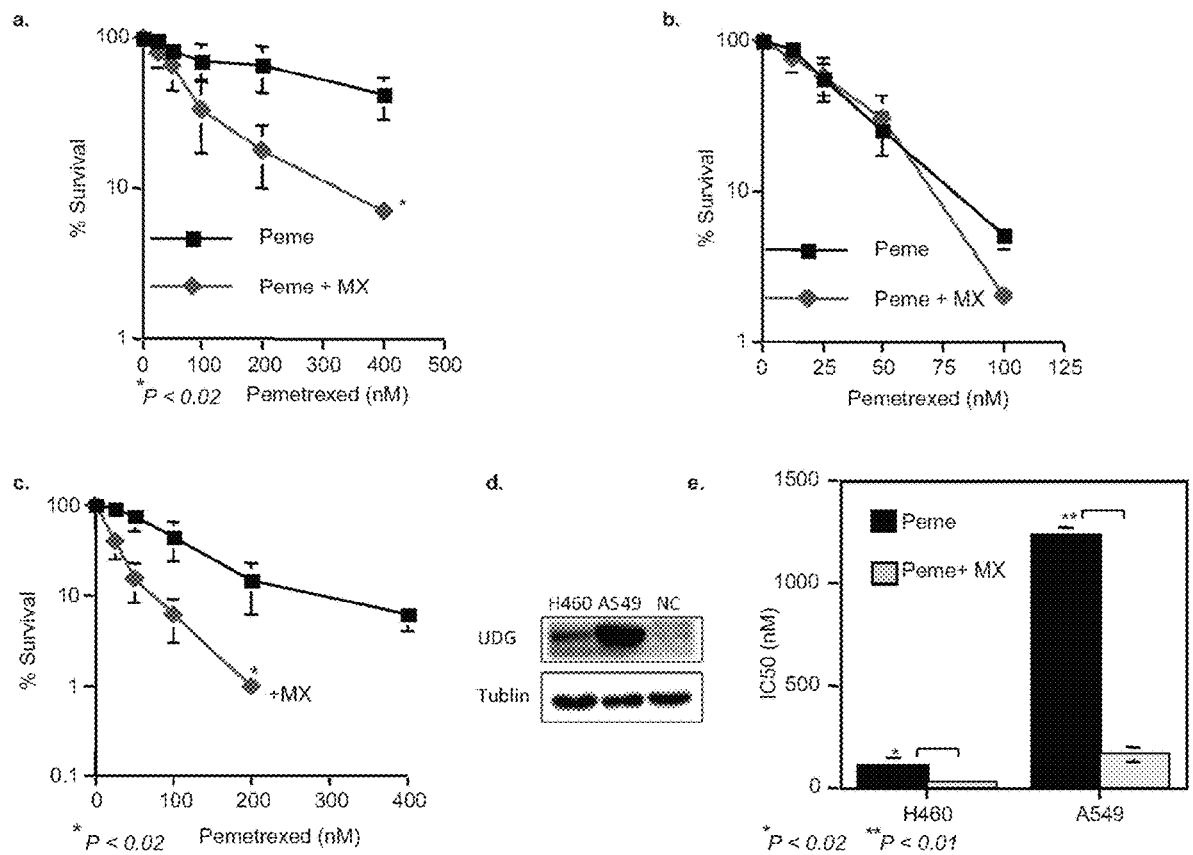
Figs. 5A-E

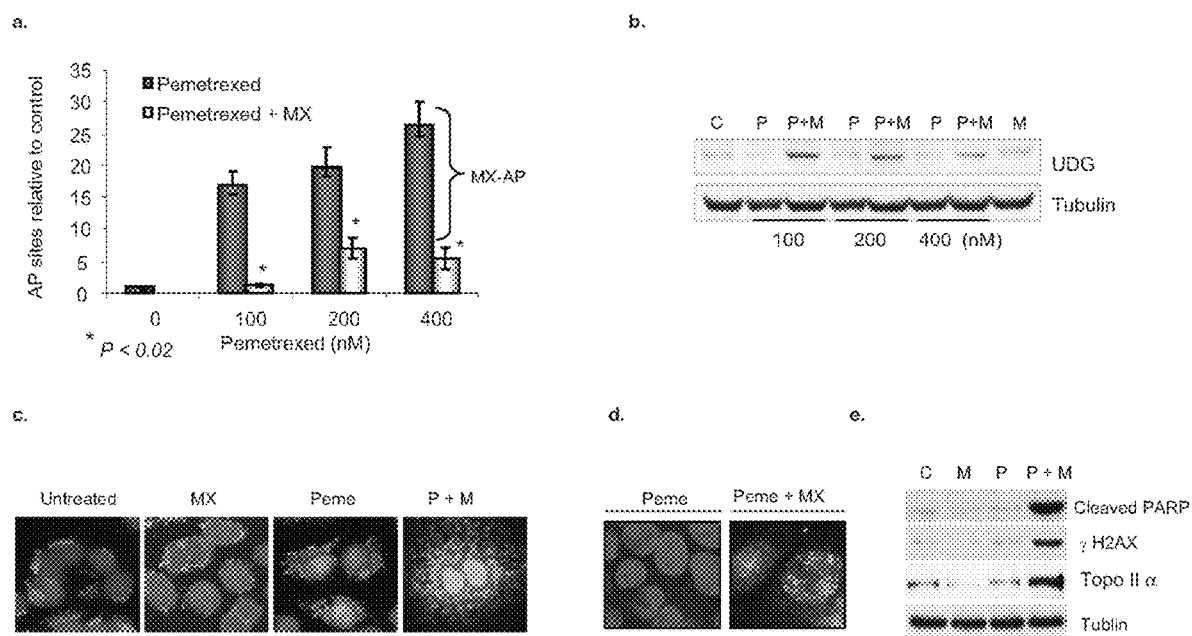
Figs. 6A-E

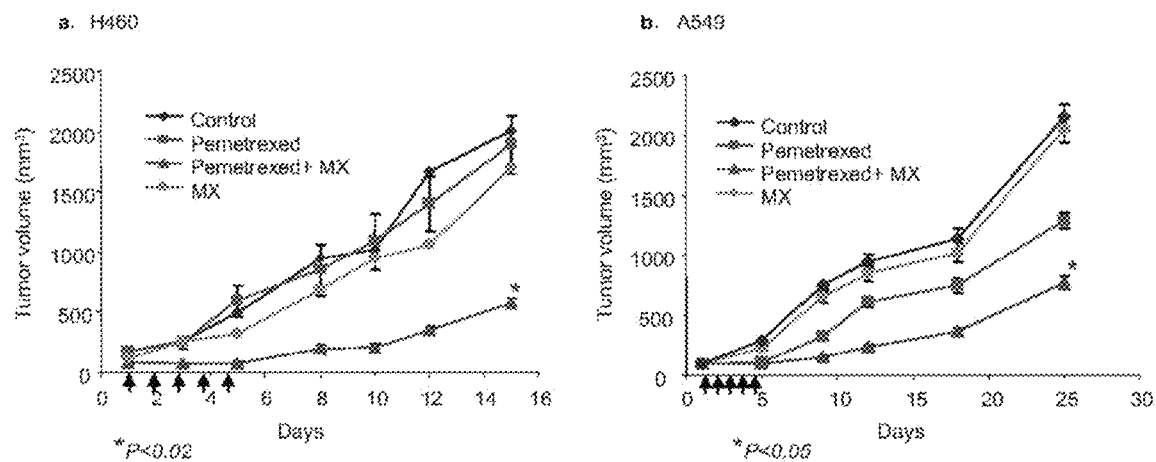
Figs. 7A-B

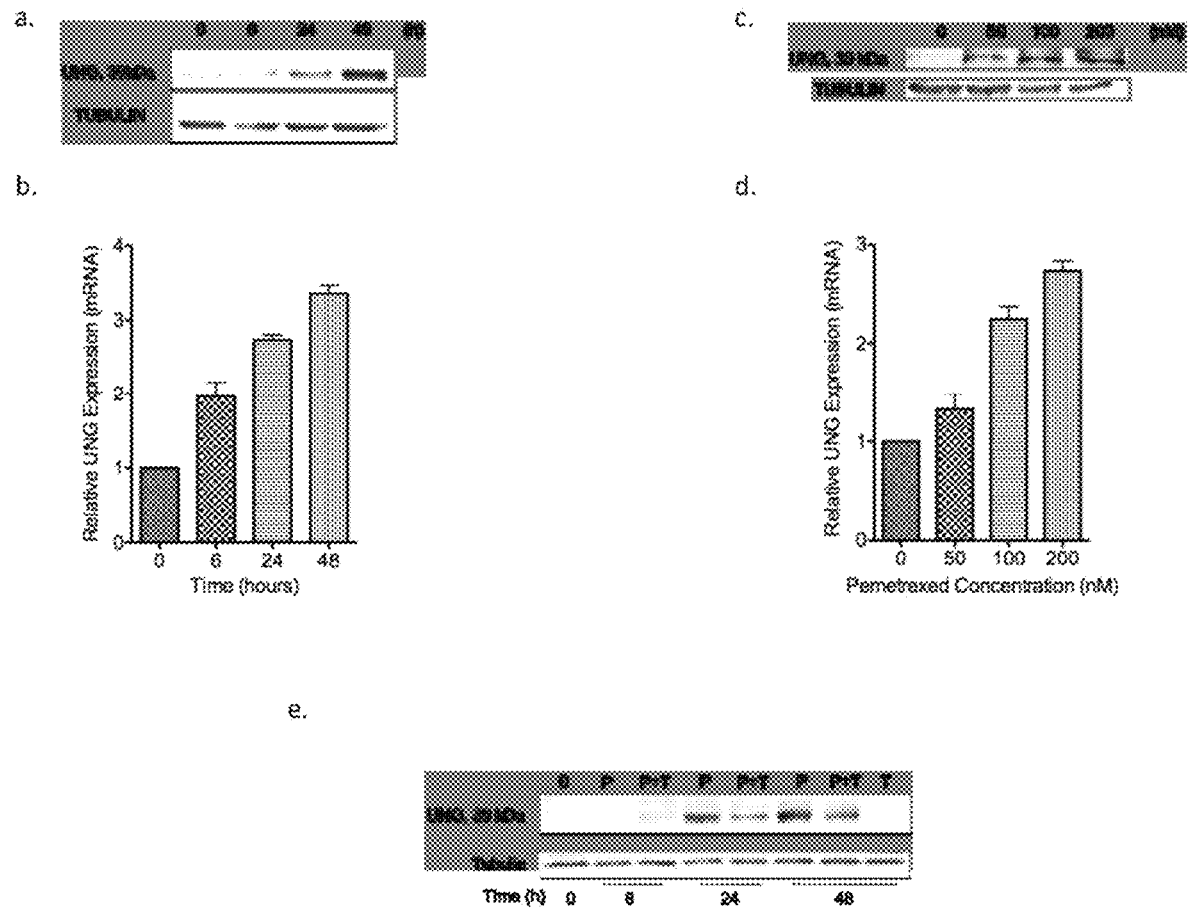
Figs. 8A-E

METHODS OF DIAGNOSING AND TREATING CANCER

RELATED APPLICATION

This application claims priority from U.S. Provisional Application No. 61/650,305, filed May 22, 2012, the subject matter of which is incorporated herein by reference in its entirety.

TECHNICAL FIELD

This application relates generally to methods for treating neoplastic disorders in a subject, and more particularly relates to the use of methods of determining the susceptibility of certain cancer and/or solid tumors in a subject to antimetabolite antineoplastic agents and base excision repair inhibitors.

BACKGROUND

Cancer is a worldwide problem. Finding novel compositions and methods for treating cancer is of interest. The treatment of cancer falls into three general categories: chemotherapy, radiation therapy and surgery. Often, therapies are combined since a combination of therapies increases the probability the cancer will be eradicated as compared to treatment strategies utilizing a single therapy. Typically, the surgical excision of large tumor masses is followed by chemotherapy and/or radiation therapy.

Chemotherapeutic agents can work in a number of ways. For example, chemotherapeutics can work by interfering with cell cycle progression or by generating DNA strand breaks. If the cancer cell is not able to overcome the cell cycle blockage or cell injury caused by the therapeutic compound, the cell will often die via apoptotic mechanisms. The use of a single chemotherapeutic agent in the treatment of cancer, with or without surgery or radiation, has several disadvantages. Commonly, cancer cells develop resistance to the chemotherapeutic agent. Such resistance results either in the requirement for higher dosages of the drug and/or the renewed spread of the cancer. Chemotherapeutic agents can be toxic to the patient. Therefore, there is a practical upper limit to the amount that a patient can receive. However, if a second agent can be developed to inhibit the pathway causing resistance, cancer cells may become susceptible to the effects of the chemotherapeutic agent.

The design of a drug to overcome resistance to the chemotherapeutic treatment of cancer should be approached with the goals of 1) finding a combination that reverses resistance and not merely improves the activity of the chemotherapeutic with respect to activity on the tumor, and 2) finding a second drug that does not potentiate the toxic effects of the first chemotherapeutic agent. These conditions require a great deal of empirical testing of agents known to have anticancer properties with agents that either may have anticancer properties, or that may augment the first agent in other ways. Unfortunately, such approaches have thus far proven largely unsuccessful for combinations of many anticancer agents. Therefore, there exist insufficient therapies that reverse resistance to chemotherapy for the treatment of cancer.

SUMMARY

Embodiments described herein relate to a method of determining the susceptibility, resistance, and/or sensitivity of a cancer in a subject to treatment with an antimetabolite agent that induces or promotes incorporation of a UDG substrate, such as uracil, into DNA of the cancer cells. The method includes obtaining a sample of cancer cells from the subject, measuring the level of UDG expression in the cancer cells, comparing the measured level of UDG expression in the cancer cells to a control level, and identifying the cancer is less susceptible to treatment with the antimetabolite agent if there is an increase in the measured levels of UDG expression in the cancer cells compared to a control level.

In some embodiments, the cancer can include carcinomas, melanomas, sarcomas, lymphomas, leukemias, astrocytomas, gliomas, malignant melanomas, chronic lymphocytic leukemia, lung cancers, colorectal cancers, ovarian cancers, pancreatic cancers, renal cancers, endometrial cancers, gastric cancers, liver cancers, head and neck cancers, breast cancer, and human non-small cell lung cancer.

In other embodiments, the antimetabolite agent can include at least one of a thymidylate synthase inhibitor, antifolate agent, or a pyrmidine analogue. For example, the antimetabolite agent can be selected from the group consisting of pemetrexed, fludarabine, 5-fluorouracil, raltitrexed, nolatrexed, and floxuridine.

Other embodiments described herein relate to a method of treating cancer in a subject. The method includes obtaining a sample of cancer cells from the subject. The level of UDG expression in the cancer cells is then measured. The measured levels of UDG expression in the cancer cells is then compared to a control level. An antimetabolite agent that induces or promotes incorporation of a UDG substrate, such as uracil, into DNA of cancer cells is administered to the subject if the measured level of UDG expression is decreased compared to a control level or an antimetabolite agent in combination with an AP endonuclease inhibitor is administered to the subject if the measured level of UDG expression is increased compared to a control level.

In some embodiments, the cancer can include carcinomas, melanomas, sarcomas, lymphomas, leukemias, astrocytomas, gliomas, malignant melanomas, chronic lymphocytic leukemia, lung cancers, colorectal cancers, ovarian cancers, pancreatic cancers, renal cancers, endometrial cancers, gastric cancers, liver cancers, head and neck cancers, and breast cancers. In a particular embodiment, the cancer is human non-small cell lung cancer.

In other embodiments, the antimetabolite agent includes at least one of a thymidylate synthase inhibitor, antifolate agent, or a pyrmidine analogue. In certain embodiments, the antimetabolite is selected from the group consisting of pemetrexed, fludarabine, 5-fluorouracil, raltitrexed, nolatrexed, and floxuridine.

In other embodiments, the AP endonuclease inhibitor is administered at an amount effective to potentiate the cytotoxicity of the antimetabolite agent administered to the cancer cells. The AP endonuclease inhibitor can include, for example, methoxyamine.

In still other embodiments, the cancer is human lung cancer, breast cancer, colorectal cancer, cervical cancer, leukemia, non-Hodgkin's lymphoma, or non-small cell lung cancer.

BRIEF DESCRIPTION OF THE DRAWINGS

FIGS. 1(A-E) illustrate that UDG activity determines the levels of uracil and AP sites in DNA. (A) UDG activity assay in vitro. Oligonucleotide duplexes containing U:G were incubated with cell extracts (5-10 μg) from $UDG^{+/+}$, DLD1flag and UDG−/− cells at 37° C. for 1 hr. Reaction products were resolved by electrophoresis through denaturing 20% polyacrylamide gels. (B) Incorporated uracil detected in UDG+/+ and UDG−/− cells by HPLC/MS/MS analysis. Cells were treated with pemetrexed (10 μM) for 6, 24, 48, and 72 hr. Cells were harvested and 40 μg of extracted DNA were in vitro reacted with purified UDG (10 U) for 2 hr. (C) Cells were treated with 5-FU (10 μM) for 6, 24, 48, and 72 hr. Uracil was quantified in the reaction product by LC-MS analysis. (D) AP site formed by pemetrexed in UDG+/+ and UDG−/− cells. Cells were treated with pemetrexed (0-400 nM) for 24 hrs. DNA was extracted and AP sites measured by ARP reagent. (E) AP site detected in DNA of UDG−/− cells after reacted with purified UDG in vitro. Cells were treated with pemetrexed (0-100 nM) for 24 hr and 40 μg DNA extracted from cells was in vitro reacted with purified UDG (10 U) for 2 hr and AP sites were measured using ARP. Results are representative of three independent experiments.

FIGS. 2(A-D) illustrate a comparison of cell sensitivity to chemotherapeutic agents between UDG+/+ and UDG−/− cells. The cytotoxicity induced by different chemotherapeutic agents was analyzed by clonogenic formation assay in UDG proficient or deficient (A) Pemetrexed treatment (0-400 nM); (B) 5-FU treatment (0-20 μM); (C) Temozolomide treatment (0-1500 μM); (D) Cisplatin treatment (0-40 μM). Results are representative of three independent experiments.

FIGS. 3(A-D) illustrate cellular response to uracil-DNA induced by pemetrexed. Comparison of cell cycle progression before and after treatment with pemetrexed between (A) UDG−/− and (B) UDG+/+. Protein alterations in the response to DNA damage, cell cycle progression, and cell death were detected in (C) UDG−/− cells and (d) UDG+/+ cells treated with pemetrexed (25 nM). Cells were collected at 6 and 24 hr after pemetrexed treatment. Results are representative of two independent experiments.

FIGS. 4(A-D) illustrate inhibition of DNA replication induced by pemetrexed. (A) Schematic diagram of the CldU, pemetrexed and IdU pulse treatments. (B) UDG−/− cells and (C) UDG+/+ cells were fixed at 6 and 24 hr after treatments and subjected to fluorescent immunostaining. Replication foci were labeled with CldU (green) and IdU (red). Results are representative of two independent experiments.

FIGS. 5(A-E) illustrate the potentiation of pemetrexed cytotoxicity by MX. (A-B) Cytotoxicity of pemetrexed alone and in combination with MX was examined by a clonogenic survival assay in UDG+/+ cells and UDG−/− cells. (C) MX potentiated the cytotoxicity of pemetrexed in H460 cells. (D) Comparison of UDG protein levels between H460 and A549 by western blotting assay. (E) Comparison of sensitivity to pemetrexed between H460 and A549 cells. Results are representative of three independent experiments.

FIGS. 6(A-E) illustrate MX-bound AP sites induced by the combination of pemetrexed and MX are lethal DNA lesions. (A) The dose-dependent relationship between the levels of AP-sites and the concentrations of pemetrexed. The AP sites in DNA were measured using ARP reagent after H460 cells were treated with pemetrexed alone (0-400 nM) or in combination with MX (6 mM) for 24 hrs. MX-bound AP sites were determined by the differences between AP sites induced by pemetrexed alone and the combination of pemetrexed and MX. (B) UDG-induction detected in cells treated with the pemetrexed alone and in combination with MX. Cells were collected and UDG protein was measured by western blotting analysis. (C) H460 cells grown on the coverslip were treated with pemetrexed alone (100 nM) and in combination with MX (6 mM) for 24 hr and subjective to the fluorescent immune-staining. The signal of UDG protein (green) was significantly enhanced and localized in nucleus (blue) of cells treated with the combination of pemetrexed and MX. (D) γH2AX foci formation detected in H460 cells treated with pemetrexed (100 nM) alone and in combination with MX (6 mM) for 24 hr; (E) Induction of the cleaved PARP and γH2AX proteins was detected by western blotting in cells with the same treatments.

FIGS. 7(A-B) illustrates MX synergistically enhances antitumor effect of pemetrexed. Human non-small cell lung cancer xenografts were grown in athymic nude mice. When tumor volume of H460 (A) or A549 (B) reached 100 mm$^3$, mice received the treatment with PBS (control), MX (4 mg/kg), pemetrexed (150 mg/kg), and pemetrexed plus MX, i.p injection/daily for 5 days. Tumor volume was measured and used to determine the therapeutic effect.

FIGS. 8 (A-E) illustrate induction of UNG in response to acute pemetrexed exposure. Time dependent changes in UNG protein (a) and mRNA (b) expression in H460 cells treated with 200 nM pemetrexed. Dose-dependent changes in UNG protein (c) and mRNA (d) expression in H460 cells treated with 0-200 nM pemetrexed for 48 h. (e) UNG expression in H460 cells treated with 200 nM pemetrexed and 10 μM thymidine alone or in combination for 6, 24 and 48 h.

DETAILED DESCRIPTION

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular*, 5th Edition, Springer-Verlag: New York, 1991, and Lewin, *Genes V*, Oxford University Press: New York, 1994.

Unless indicated otherwise, the following terms have the following meanings when used herein and in the appended claims. Those terms that are not defined below or elsewhere in the specification shall have their art-recognized meaning.

As used in the specification and the appended claims, the singular forms "a," "an" and "the" include plural referents unless the context clearly dictates otherwise. Thus, for example, reference to "a substituent" includes a single substituent as well as two or more substituents that may be the same or different, reference to "a compound" encompasses a combination or mixture of different compounds as well as a single compound, reference to "a pharmaceutically acceptable carrier" includes two or more such carriers as well as a single carrier, and the like.

The term "agent" and "drug" are used herein to mean chemical compounds, mixtures of chemical compounds, biological macromolecules, or extracts made from biological materials, such as bacteria, plants, fungi, or animal particularly mammalian) cells or tissues that are suspected of having therapeutic properties. The agent or drug may be purified, substantially purified, or partially purified.

The term "antimetabolite" is used herein to mean a chemotherapeutic with a similar structure to a substance (a metabolite e.g., nucleoside) required for normal biochemical reactions, yet different enough to interfere with the normal functions of cells, including cell division.

The term "antineoplastic" is used herein to mean a chemotherapeutic intended to inhibit or prevent the maturation and proliferation of neoplasms (tumors) that may become malignant, by targeting the DNA.

The terms "array", "micro-array", and "biochip" are used herein interchangeably. They refer to an arrangement, on a substrate surface, of hybridizable array elements, preferably, multiple nucleic acid molecules of known sequences. Each nucleic acid molecule is immobilized to a discrete spot (i.e., a defined location or assigned position) on the substrate surface. The term "micro-array" more specifically refers to an array that is miniaturized so as to require microscopic examination for visual evaluation.

The term "biological sample" is used herein in its broadest sense. A biological sample may be obtained from a subject (e.g., a human) or from components (e.g., tissues) of a subject. The sample may be of any biological tissue that includes cancer cells. Frequently, the sample will be a "clinical sample", i.e., a sample derived from a patient. Such samples include, but are not limited to, bodily fluids which may contain cancer cells, e.g., blood; tissue or fine needle biopsy samples, lung tissue; and archival samples with known diagnosis, treatment and/or outcome history. Biological samples may also include sections of tissues or cells, such as frozen sections taken from histological purposes. The term biological sample also encompasses any material derived by processing the biological sample. Derived materials include, but are not limited to, cells (or their progeny) isolated from the sample, proteins or nucleic acid molecules extracted from the sample. Processing of the biological sample may involve one or more of, filtration, distillation, extraction, concentration, inactivation of interfering components, addition of reagents, and the like.

The term "control sample" refers to one or more biological samples isolated from an individual or group of individuals that are normal (i.e., healthy).

The term "decreased level of expression" as used herein, refers to a decrease in expression of a polynucleotide, e.g., gene, RNA, DNA, or protein at least 10% or more. For example, 20%, 30%, 40%, or 50%, 60%, 70%, 80%, 90% or more, or a decrease in expression of greater than 1-fold, 2-fold, 3-fold, 4-fold, 5-fold, 10-fold, 50-fold, 100-fold or more as measured by one or more methods described herein. The term "increased level of expression" as used herein, refers to an increase in expression of a polynucleotide, e.g., gene, RNA, DNA, or protein at least 10% or more. For example, 20%, 30%, 40%, or 50%, 60%, 70%, 80%, 90% or more or an increase in expression of greater than 1-fold, 2-fold, 3-fold, 4-fold, 5-fold, 10-fold, 50-fold, 100-fold or more as measured by one or more methods, such as method described herein.

The term "diagnosis" refers to a process aimed at determining if an individual is afflicted with a disease or ailment.

The term "hybridizing" refers to the binding of two single stranded nucleic acids via complementary base pairing. The term "specific hybridization" refers to a process in which a nucleic acid molecule preferentially binds, duplexes, or hybridizes to a particular nucleic acid sequence under stringent conditions (e.g., in the presence of competitor nucleic acids with a lower degree of complementarity to the hybridizing strand). In certain embodiments of the present invention, these terms more specifically refer to a process in which a nucleic acid fragment (or segment) from a test sample preferentially binds to a particular probe and to a lesser extent or not at all, to other probes, for example, when these probes are immobilized on an array.

The terms "labeled", "labeled with a detectable agent" and "labeled with a detectable moiety" are used herein interchangeably. These terms are used to specify that an entity (e.g., a probe) can be visualized, for example, following binding to another entity (e.g., a polynucleotide or polypeptide). Preferably, the detectable agent or moiety is selected such that it generates a signal which can be measured and whose intensity is related to the amount of bound entity. In array-based methods, the detectable agent or moiety is also preferably selected such that it generates a localized signal, thereby allowing spatial resolution of the signal from each spot on the array. Methods for labeling polypeptides or polynucleotides are well-known in the art. Labeled polypeptides or polynucleotides can be prepared by incorporation of or conjugation to a label, that is directly or indirectly detectable by spectroscopic, photochemical, biochemical, immunochemical, electrical, optical, or chemical means. Suitable detectable agents include, but are not limited to, various ligands, radionuclides, fluorescent dyes, chemiluminescent agents, microparticles, enzymes, calorimetric labels, magnetic labels, and haptens. Detectable moieties can also be biological molecules such as molecular beacons and aptamer beacons.

The term "morphology" is used herein to mean the visual appearance of a cell or organism when viewed with the eye, a light microscope, a confocal microscope or an electron microscope, as appropriate.

The terms "normal" and "healthy" are used herein interchangeably. They refer to an individual or group of individuals who have not shown to have cancer or tumors. In certain embodiments, normal individuals have similar sex, age, body mass index as compared with the individual from which the sample to be tested was obtained. The term "normal" is also used herein to qualify a sample isolated from a healthy individual.

The terms "nucleic acid molecule" and "polynucleotide" are used herein interchangeably. They refer to a deoxyribonucleotide or ribonucleotide polymer in either single- or double-stranded form, and unless otherwise stated, encompass known analogs of natural nucleotides that can function in a similar manner as naturally occurring nucleotides. The terms encompass nucleic acid-like structures with synthetic backbones, as well as amplification products.

The term "probe", as used herein, refers to a nucleic acid molecule of known sequence, which can be a short DNA sequence (i.e., an oligonucleotide), a PCR product, or mRNA isolate. Probes are specific DNA sequences to which nucleic acid fragments from a test sample are hybridized. Probes specifically bind to nucleic acids of complementary or substantially complementary sequence through one or more types of chemical bonds, usually through hydrogen bond formation.

The terms "protein", "polypeptide", and "peptide" are used herein interchangeably, and refer to amino acid sequences of a variety of lengths, either in their neutral (uncharged) forms or as salts, and either unmodified or modified by glycosylation, side chain oxidation, or phosphorylation. In certain embodiments, the amino acid sequence is the full-length native protein. In other embodiments, the amino acid sequence is a smaller fragment of the full-length protein. In still other embodiments, the amino acid sequence is modified by additional substituents attached to the amino acid side chains, such as glycosyl units, lipids, or inorganic ions such as phosphates, as well as modifications relating to chemical conversion of the chains, such as oxidation of sulfhydryl groups. Thus, the term "protein" (or its equivalent terms) is intended to include the amino acid sequence of the full-length native protein, subject to those modifications that do not change its specific properties. In particular, the term "protein" encompasses protein isoforms, i.e., variants that are encoded by the same gene, but that differ in their pI or MW, or both. Such isoforms can differ in their amino acid sequence (e.g., as a result of alternative splicing or limited proteolysis), or in the alternative, may arise from differential post-translational modification (e.g., glycosylation, acylation, phosphorylation).

The term "protein analog", as used herein, refers to a polypeptide that possesses a similar or identical function as the full-length native protein but need not necessarily comprise an amino acid sequence that is similar or identical to the amino acid sequence of the protein, or possesses a structure that is similar or identical to that of the protein. Preferably, in the context of the present invention, a protein analog has an amino acid sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the amino acid sequence of the full-length native protein.

The term "protein fragment", as used herein, refers to a polypeptide comprising an amino acid sequence of at least 4 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino acid residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of a second polypeptide. The fragment of a marker protein may or may not possess a functional activity of the full-length native protein.

The term "subject," "individual," and "patient" are used interchangeably herein to mean a human or other animal, such as farm animals or laboratory animals (e.g., guinea pig or mice) capable of having cell cycle (influenced) determined diseases, either naturally occurring or induced, including but not limited to cancer.

The term "reverses resistance" means that the use of a second agent in combination with a primary chemotherapeutic is able to produce a significant decrease in tumor volume at a level of statistical significance (e.g., $p<0.05$) when compared to tumor volume of untreated tumor in the circumstance where the primary chemotherapeutic alone is unable to produce a statistically significant decrease in tumor volume compared to tumor volume of untreated tumor. This generally applies to tumor volume measurements made at a time when the untreated tumor is growing log rhythmically.

The term "potentiate" as used herein means to enhance or increase the beneficial activity or efficacy of the anticancer agent over that which would be expected from the anticancer agent alone or the potentiating agent alone.

The term "sensitize" as used herein means to alter cancer cells or tumor cells in a way that allows for more effective treatment of the associated neoplastic disease with an antimetabolite agent, an anticancer agent, or radiation therapy. In some embodiments, normal cells are not affected to an extent that causes the normal cells to be unduly injured by the antimetabolite, chemotherapy, or radiation therapy.

The term "subject" and "individual" are used herein interchangeably. They refer to a human or another mammal (e.g., primate, dog, cat, goat, horse, pig, mouse, rat, rabbit, and the like), that can be afflicted with cancer, but may or may not have the disease. In many embodiments, the subject is a human being.

The term "synergistic effect" as used herein means the combined effect of two or more anticancer agents or chemotherapy drugs can be greater than the sum of the separate effects of the anticancer agents or chemotherapy drugs alone.

The term "therapeutically effective amount" means the amount of the subject compound that will elicit a desired response, for example, a biological or medical response of a tissue, system, animal, or human that is sought, for example, by a researcher, veterinarian, medical doctor, or other clinician.

The terms "uracil DNA glycosylose" or "UDG" or "UNG" refer to a conserved DNA repair protein expressed in all types of human cells. It specifically removes uracil from DNA and protect cells from cytotoxicity and mutagenicity. Human UDG is encoded by the UNG gene. Alternative promoter usage and splicing of this gene produces two different isoforms: the mitochondrial UNG1 and the nuclear UNG2. Nuclear UDG (UNG2) is the predominant form in cells and represents greater than 90% of the total enzyme activity.

The term "wild type" (wt) cell or cell line is used herein, for purposes of the specification and claims, to mean a cell or cell line that retains the characteristics normally associated with that type of cell or cell line for the physiological process or morphological characteristic that is being examined. It is permissible for the cell or cell line to have non-wild type characteristics for physiological process or morphological characteristics that are not being examined as long as they do not appreciably affect the process or characteristic being examined.

Embodiments described herein relate to methods of determining the susceptibility, resistance, and/or sensitivity of a cancer in a subject to treatment with an antimetabolite agent that induces or promotes incorporation of a UDG substrate, such as uracil, into DNA of the cancer cells, by determining the level of UDG expression in the cancer cells of the subject. UDG substrates, such as uracil and/or 2-fluoroadenine 9-β-Darbinofuranoside-triphosphate) can be incorporated into DNA of cancer cells by administering antimetabolite agents to the cancer cells. The UDG substrates can serve as a poor substrate for DNA replication enzymes, leading to the inhibition of DNA replication, chain termination, and loss of genome integrity. To maintain the genome integrity of the cancer cells, the cancer cells rapidly eliminate the UDG substrate from the DNA by base excision repair, which is initiated by the uracil-DNA-glycosylase (UDG or UNG) enzyme.

The UDG enzyme hydrolyzes the N-glycosidic bond between the UDG substrate (e.g., uracil residue) and the deoxyribose sugar of the DNA backbone, liberating the UDG substrate and generating an abasic site (e.g., an apurinic or apyrimidinic (AP) site). An apurinic or apyrimidinic (AP) site results from the loss of a purine or pyrimidine residue, respectively, from DNA (deoxyribonucleic acid). The AP site is further processed by a 5'-3' endonuclease (AP endonuclease (APE)) that incises the phosphodiester bond on both sides of the damaged purine or pyrimidine base. The AP endonucleases can introduce chain breaks by cleaving the phosphodiester bonds at the AP sites.

It was found that UDG directed base excision repair (BER) plays significant role in resistance of cancers to antimetabolite therapy. The level of UDG expression by the cancer cells was found to correlate directly with antimetabolite $IC_{50}$ of the cancer cells. Other DNA glycosylases were found to not be significantly associated with antimetabolite sensitivity suggesting UDG is the major glycosylase for uracil removal in antimetabolite-treated cells.

Advantageously, the identification of UDG expression as a predictive marker for antimetabolite resistance can be used to potentiate antimetabolite efficacy via BER inhibition. It was further found that AP endonuclease inhibition of UDG induced BER restores antimetabolite sensitivity in cancer cells expressing increased levels of UDG. Antimetabolite/AP endonuclease inhibitor combinations can also be used to overcome antimetabolite insensitivity in certain cancer subtypes and to restore sensitivity in cells that acquire resistance due to chronic antimetabolite exposure. Therefore, tailoring chemotherapy based on histological subtype and UDG expression can be used as a favorable strategy for aggressive, treatment-refractory malignancies, such as cancer (e.g., lung cancer).

In some embodiments, the level of UDG expression in the cancer cells of the subject can be determined by obtaining a sample of cancer cells from the subject diagnosed with cancer and measuring the level of UDG expression in the cancer cells. The cancer can be selected from the group consisting of carcinomas, melanomas, sarcomas, lymphomas, leukemias, astrocytomas, gliomas, malignant melanomas, chronic lymphocytic leukemia, lung cancers, prostate cancer, colorectal cancers, ovarian cancers, pancreatic cancers, renal cancers, endometrial cancers, gastric cancers, liver cancers, head and neck cancers.

In some embodiments, the cancer is a cancer or tumor in which UDG is expressed or over expressed compared to normal cells or other cancers. It was found that UDG is expressed in several types of human tumors at higher levels than corresponding normal cells and at least some other cancers. Cancers or cancer cells that have a high UDG expression level compared to normal cells can include lung cancer, including non-small cell lung cancer cells, lymphoma, chronic lymphotic leukemia, mesilthelioma, colorectal cancer, pancreatic cancer, breast cancer, cervical cancer, leukemia, and non-Hodgkin's lymphoma.

The samples used in the practice of the inventive methods may be fresh or frozen samples collected from a subject, or archival samples. Biological samples may be collected by any non-invasive means, such as, for example, by drawing blood from a subject, or using fine needle aspiration or needle biopsy. Alternatively, biological samples may be collected by an invasive method, including, for example, surgical biopsy.

In certain embodiments, the inventive methods are performed on the biological sample itself without or with limited processing of the sample.

In other embodiments, the inventive methods are performed at the single cell level (e.g., isolation of cells from a biological sample). However, in such embodiments, the inventive methods are preferably performed using a sample comprising many cells, where the assay is "averaging" expression over the entire collection of cells present in the sample. Preferably, there is enough of the biological sample to accurately and reliably determine the expression of UDG. Multiple biological samples may be taken from the same tissue/body part in order to obtain a representative sampling of the tissue.

In still other embodiments, the level of UDG expression can be measured in a protein extract prepared from cancer cells of a biological sample. The protein extract can contain the total UDG content by the cancer cell or cells. Methods of protein extraction are well known in the art (see, for example "Protein Methods", D. M. Bollag et al., 2nd Ed., 1996, Wiley-Liss; "Protein Purification Methods: A Practical Approach", E. L. Harris and S. Angal (Eds.), 1989; "Protein Purification Techniques: A Practical Approach", S. Roe, 2nd Ed., 2001, Oxford University Press; "Principles and Reactions o/Protein Extraction, Purification, and Characterization", H. Ahmed, 2005, CRC Press: Boca Raton, Fla.). Numerous different and versatile kits can be used to extract proteins from cells, and are commercially available from, for example, BioRad Laboratories (Hercules, Calif.), BD Biosciences Clontech (Mountain View, Calif.), Chemicon International, Inc. (Temecula, Calif.), Calbiochem (San Diego, Calif.), Pierce Biotechnology (Rockford, Ill.), and Invitrogen Corp. (Carlsbad, Calif.). User Guides that describe in great detail the protocol to be followed are usually included in all these kits. Sensitivity, processing time and costs may be different from one kit to another. One of ordinary skill in the art can easily select the kits) most appropriate for a particular situation. After the protein extract has been obtained, the protein concentration of the extract can be standardized to a value being the same as that of the control sample in order to allow signals of the UDG expression to be quantitated. Such standardization can be made using photometric or spectrometric methods or gel electrophoresis.

In yet other embodiments, the level of UDG expression can be measured from nucleic acid molecules extracted from cancer cells of a biological sample. For example, RNA may be extracted from the sample before analysis. Methods of RNA extraction are well known in the art (see, for example, J. Sambrook et al., "Molecular Cloning: A Laboratory Manual", 1989, 2nd Ed., Cold Spring Harbor Laboratory Press: Cold Spring Harbor, N.Y.). Most methods of RNA isolation from cells are based on the disruption of the tissue in the presence of protein denaturants to quickly and effectively inactivate RNAses. Isolated total RNA may then be further purified from the protein contaminants and concentrated by selective ethanol precipitations, phenol/chloroform extractions followed by isopropanol precipitation or cesium chloride, lithium chloride or cesium trifluoroacetate gradient centrifugations. Kits are also available to extract RNA (i.e., total RNA or mRNA) from bodily fluids or tissues and are commercially available from, for example, Ambion, Inc. (Austin, Tex.), Amersham Biosciences (Piscataway, N.J.), BD Biosciences Clontech (Palo Alto, Calif.), BioRad Laboratories (Hercules, Calif.), GIBCO BRL (Galthersburg, Md.), and Qiagen, Inc. (Valencia, Calif.).

In certain embodiments, after extraction, mRNA is amplified, and transcribed into cDNA, which can then serve as template for multiple rounds of transcription by the appropriate RNA polymerase. Amplification methods are well known in the art (see, for example, A. R. Kimmel and S. L. Berger, Methods Enzymol. 1987, 152: 307-316; J. Sambrook et al., "Molecular Cloning: A Laboratory Manual", 1989, 2nd Ed., Cold Spring Harbour Laboratory Press: New York; "Short Protocols in Molecular Biology", F. M. Ausubel (Ed.), 2002, 5th Ed., John Wiley & Sons; U.S. Pat. Nos. 4,683,195; 4,683,202 and 4,800,159). Reverse transcription reactions may be carried out using non-specific primers, such as an anchored oligo-dT primer, or random sequence primers, or using a target-specific primer complementary to the RNA, or using thermostable DNApolymerases (such as avian myeloblastosis virus reverse transcriptase or Moloney murine leukemia virus reverse transcriptase).

In general, UDG expression levels in the cancer cells can be determined by contacting cancer cells in a biological sample isolated from a subject with binding agents for UDG; detecting, in the sample, the levels of UDG that bind to the binding agents; and comparing the levels of UDG in the sample with the levels of UDG in a control sample. As used herein, the term "binding agent" refers to an entity, such as a polypeptide or antibody that specifically binds to UDG. An entity "specifically binds" to UDG if it reacts/interacts at a detectable level with UDG but does not react/interact detectably with peptides containing unrelated sequences or sequences of different polypeptides.

In certain embodiments, the binding agent is an RNA molecule, or a polypeptide (e.g., a polypeptide that comprises a polypeptide sequence of a protein marker, a peptide variant thereof, or a non-peptide mimetic of such a sequence).

In other embodiments, the binding agent is an antibody specific for UDG. Antibodies for use in the methods include monoclonal and polyclonal antibodies, immunologically active fragments (e.g., Fab or (Fab)2 fragments), antibody heavy chains, humanized antibodies, antibody light chains, and chimeric antibodies. Antibodies, including monoclonal and polyclonal antibodies, fragments and chimeras, may be prepared using methods known in the art (see, for example, R. G. Mage and E. Lamoyi, in "Monoclonal Antibody Production Techniques and Applications", 1987, Marcel Dekker, Inc.: New York, pp. 79-97; G. Kohler and C. Milstein, Nature, 1975, 256: 495-497; D. Kozbor et al., J. Immunol. Methods, 1985, 81: 31-42; and R. J. Cote et al., Proc. Natl. Acad. Sci. 1983, 80: 2026-203; R. A. Lerner, Nature, 1982, 299: 593-596; A. C. Nairn et al., Nature, 1982, 299: 734-736; A. J. Czernik et al., Methods Enzymol. 1991, 201: 264-283; A. J. Czernik et al., Neuromethods: Regulatory Protein Modification: Techniques & Protocols, 1997, 30: 219-250; A. J. Czemik et al., NeuroNeuroprotocols, 1995, 6: 56-61; H. Zhang et al., J. Biol. Chem. 2002, 277: 39379-39387; S. L. Morrison et al., Proc. Natl. Acad. Sci., 1984, 81: 6851-6855; M. S, Neuberger et al., Nature, 1984, 312: 604-608; S. Takeda et al., Nature, 1985, 314: 452-454). Antibodies to be used in the methods can be purified by methods well known in the art (see, for example, S. A. Minden, "Monoclonal Antibody Purification", 1996, IBC Biomedical Library Series: Southbridge, Mass.). For example, antibodies can be affinity purified by passage over a column to which a protein marker or fragment thereof is bound. The bound antibodies can then be eluted from the column using a buffer with a high salt concentration.

Instead of being prepared, antibodies to be used in the methods invention may be obtained from scientific or commercial sources.

In certain embodiments, the binding agent is directly or indirectly labeled with a detectable moiety. The role of a detectable agent is to facilitate the measuring of the UDG expression levels by allowing visualization of the complex formed by binding of the binding agent to UDG (or analog or fragment thereof). The detectable agent can be selected such that it generates a signal which can be measured and whose intensity is related (preferably proportional) to the amount of UDG present in the sample being analyzed. Methods for labeling biological molecules such as polypeptides and antibodies are well-known in the art (see, for example, "Affinity Techniques. Enzyme Purification. Part B", Methods in Enzymol., 1974, Vol. 34, W. B. Jakoby and M. Wilneck (Eds.), Academic Press: New York, N.Y.; and M. Wilchek and E. A. Bayer, Anal. Biochem., 1988, 171: 1-32).

Any of a wide variety of detectable agents can be used in the methods described herein. Detectable agents include, but are not limited to: various ligands, radionuclides, fluorescent dyes, chemiluminescent agents, microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, and biotin, dioxigenin or other haptens and proteins for which antisera or monoclonal antibodies are available.

In certain embodiments, the binding agents (e.g., antibodies) may be immobilized on a carrier or support (e.g., a bead, a magnetic particle, a latex particle, a microtiter plate well, a cuvette, or other reaction vessel). Examples of suitable carrier or support materials include agarose, cellulose, nitrocellulose, dextran, Sephadex, Sepharose, liposomes, carboxymethyl cellulose, polyacrylamides, polystyrene, gabbros, filter paper, magnetite, ion-exchange resin, plastic film, plastic tube, glass, polyamine-methyl vinylether-maleic acid copolymer, amino acid copolymer, ethylene-maleic acid copolymer, nylon, silk, and the like. Binding agents may be indirectly immobilized using second binding agents specific for the first binding agents (e.g., mouse antibodies specific for the protein markers may be immobilized using sheep anti-mouse IgG Fc fragment specific antibody coated on the carrier or support).

UDG expression levels in the methods described herein may be determined using immunoassays. Examples of such assays are radioimmunoassays, enzyme immunoassays (e.g., ELISA), immunofluorescence immunoprecipitation, latex agglutination, hemagglutination, and histochemical tests, which are conventional methods well-known in the art. As will be appreciated by one skilled in the art, the immunoassay may be competitive or noncompetitive. Methods of detection and quantification of the signal generated by the complex formed by binding of the binding agent with the UDG will depend on the nature of the assay and of the detectable moiety (e.g., fluorescent moiety).

Alternatively, UDG expression levels may be determined using mass spectrometry based methods or image (including use of labeled ligand) based methods known in the art for the detection of proteins. Other suitable methods include proteomics-based methods. Proteomics, which studies the global changes of protein expression in a sample, typically includes the following steps: (I) separation of individual proteins in a sample by electrophoresis (2-D PAGE), (2) identification of individual proteins recovered from the gel (e.g., by mass spectrometry or N-terminal sequencing), and (3) analysis of the data using bioinformatics.

As already mentioned above, the methods described herein may involve determination of the expression levels of a set of nucleic acid molecules comprising polynucleotide sequences coding for UDG. Determination of expression levels of nucleic acid molecules in the practice of the inventive methods may be performed by any method, including, but not limited to, Southern analysis, Northern analysis, polymerase chain reaction (PCR) (see, for example, U.S. Pat. Nos. 4,683,195; 4,683,202, and 6,040, 166; "PCR Protocols: A Guide to Methods and Applications", Innis et al. (Eds.), 1990, Academic Press: New York), reverse transcriptase PCR (RT-PCT), anchored PCR, competitive PCR (see, for example, U.S. Pat. No. 5,747,251), rapid amplification of cDNA ends (RACE) (see, for example, "Gene Cloning and Analysis: Current Innovations, 1997, pp. 99-115); ligase chain reaction (LCR) (see, for example, EP 01 320308), one-sided PCR (Ohara et al., Proc. Natl. Acad. Sci., 1989, 86: 5673-5677), in situ hybridization, Taqman based assays (Holland et al., Proc. Natl. Acad. Sci., 1991, 88:7276-7280), differential display (see, for example, Liang et al., Nucl. Acid. Res., 1993, 21: 3269-3275) and other RNA fingerprinting techniques, nucleic acid sequence based amplification (NASBA) and other transcription based amplification systems (see, for example, U.S. Pat. Nos. 5,409,818 and 5,554,527), Qbeta Replicase, Strand Displacement Amplification (SDA), Repair Chain Reaction (RCR), nuclease protection assays, subtraction-based methods, Rapid-Scan™, and the like.

Nucleic acid probes for use in the detection of polynucleotide sequences in biological samples may be constructed using conventional methods known in the art. Probes may be based on nucleic acid sequences encoding at least 5 sequential amino acids from regions of nucleic acids encoding UDG, and preferably comprise about 15 to about 50 nucleotides. A nucleic acid probe may be labeled with a detectable moiety, as mentioned above in the case of binding agents. The association between the nucleic acid probe and detectable moiety can be covalent or non-covalent. Detectable moieties can be attached directly to nucleic acid probes or indirectly through a linker (E. S. Mansfield et al., Mol. Cell. Probes, 1995, 9: 145-156). Methods for labeling nucleic acid molecules are well-known in the art (for a review of labeling protocols, label detection techniques and recent developments in the field, see, for example, L. J. Kricka, Ann. Clin. Biochem. 2002, 39: 114-129; R. P. van Gijlswijk et al., Expert Rev. Mol. Diagn. 2001, 1: 81-91; and S. Joos et al., J. Biotechnol. 1994, 35:135-153).

Nucleic acid probes may be used in hybridization techniques to detect polynucleotides encoding UDG. The technique generally involves contacting an incubating nucleic acid molecules in a biological sample obtained from a subject with the nucleic acid probes under conditions such that specific hybridization takes place between the nucleic acid probes and the complementary sequences in the nucleic acid molecules. After incubation, the non-hybridized nucleic acids are removed, and the presence and amount of nucleic acids that have hybridized to the probes are detected and quantified.

Detection of nucleic acid molecules comprising polynucleotide sequences coding for UDG may involve amplification of specific polynucleotide sequences using an amplification method such as PCR, followed by analysis of the amplified molecules using techniques known in the art. Suitable primers can be routinely designed by one skilled in the art. In order to maximize hybridization under assay conditions, primers and probes employed in the methods of the invention generally have at least 60%, preferably at least 75% and more preferably at least 90% identity to a portion of nucleic acids encoding a protein marker.

Hybridization and amplification techniques described herein may be used to assay qualitative and quantitative aspects of expression of nucleic acid molecules comprising polynucleotide sequences coding for the inventive protein markers.

Alternatively, oligonucleotides or longer fragments derived from nucleic acids encoding each protein marker may be used as targets in a microarray. A number of different array configurations and methods of their production are known to those skilled in the art (see, for example, U.S. Pat. Nos. 5,445,934; 5,532,128; 5,556,752; 5,242,974; 5,384, 261; 5,405,783; 5,412,087; 5,424,186; 5,429,807; 5,436, 327; 5,472,672; 5,527,681; 5,529,756; 5,545,531; 5,554, 501; 5,561,071; 5,571,639; 5,593,839; 5,599,695; 5,624, 711; 5,658,734; and 5,700,637). Microarray technology allows for the measurement of the steady-state level of large numbers of polynucleotide sequences simultaneously. Microarrays currently in wide use include cDNA arrays and oligonucleotide arrays. Analyses using microarrays are generally based on measurements of the intensity of the signal received from a labeled probe used to detect a cDNA sequence from the sample that hybridizes to a nucleic acid probe immobilized at a known location on the microarray (see, for example, U.S. Pat. Nos. 6,004,755; 6,218,114; 6,218,122; and 6,271,002). Array-based gene expression methods are known in the art and have been described in numerous scientific publications as well as in patents (see, for example, M. Schena et al., Science, 1995, 270: 467-470; M. Schena et al., Proc. Natl. Acad. Sci. USA 1996, 93: 10614-10619; 1.1. Chen et al., Genomics, 1998, 51: 313324; U.S. Pat. Nos. 5,143,854; 5,445,934; 5,807,522; 5,837, 832; 6,040,138; 6,045,996; 6,284,460; and 6,607,885).

Once the expression levels of UDG in the cancer cells has been measured or determined (as described above), the measured level of UDG expression is compared to a control level. The control level can be based upon the level of UDG in a normal cell obtained from a control population (e.g., the general population) or a select population of subjects. For example, the select population may be comprised of apparently healthy subjects or from subjects at risk of developing cancer.

The control level can be related to the value used to characterize the level of UDG expression obtained from the subject. The control level can also take a variety of forms. For example, the control level can be a single cut-off value, such as a median or mean. The control level can be established based upon comparative groups, such as where the level in one defined group is double the level of another defined group.

Control levels of UDG expression in cells, for example, can be obtained (e.g., mean levels, median levels, or "cut-off" levels) by assaying a large sample of subjects in the general population or a select population and then using a statistical model, such as the predictive value method for selecting a positivity criterion or receiver operator characteristic curve that defines optimum specificity (highest true negative rate) and sensitivity (highest true positive rate), as described in Knapp, R. G. and Miller, M. C. (1992): *Clinical Epidemiology and Biostatistics*, William and Wilkins, Harual Publishing Co. (Malvern, Pa.).

Depending upon the level or value of measured UDG when compared to the control level, a determination can be made as to whether the cancer cells or cancer of the subject is more or less susceptible, sensitive, and/or resistance to treatment with an antimetabolite. A measured or determined expression level of UDG for the cancer higher or increased compared to the control level identifies the cancer as being less susceptible to treatment with the antimetabolite agent administered alone and hence the antimetabolite agent as being less effective in treating the cancer. In contrast, a measured or determined expression level of UDG less than the control level identifies the cancer as being more susceptible to treatment with the antimetabolite agent administered alone and hence the antimetabolite agent as being more effective in treating the lung cancer.

By determining the efficacy of an antimetabolite agent, such as pemetrexed, to treating cancer and/or susceptibility, sensitivity, and/or resistance of the cancer cell to the antimetabolite, skilled physicians may select and prescribe treatments adapted to each individual patient with increased efficiency. In some embodiments, a method of treating cancer with an antimetabolite can include first determining the level of UDG expression of cancer cells of a subject diagnosed with cancer and then administering an antimetabolite agent alone or in combination with a BER inhibitor, such as an AP endonuclease inhibitor, depending on the determined or measured level of UDG expression.

In some embodiments, an antimetabolite agent can be administered alone or without a BER inhibitor, such as an AP endonuclease inhibitor when the level of UDG expression for the cancer is lower than a control value to mitigate side-effect burdens on the patient being treated.

The antimetabolite agent can include agents, compounds, or small molecules that induce or promote incorporation of a UDG substrate, such as uracil, into DNA of cancer cells of the subject. Antimetabolite agents include, but are not limited to acanthifolic acid, aminothiadiazole, anastrozole, bicalutamide, brequinar sodium, capecitabine, carmofur, Ciba-Geigy CGP-30694, cladribine, cyclopentyl cytosine, cytarabine phosphate stearate, cytarabine conjugates, cytarabine ocfosfate, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, finasteride, floxuridine, fludarabine, fludarabine phosphate, N-(2'-furanidyl)-5-fluorouracil, Daiichi Seiyaku FO-152, fluorouracil (5-FU), 5-FU-fibrinogen, isopropyl pyrrolizine, Lilly LY-188011, Lilly LY-264618, methobenzaprim, methotrexate, Wellcome MZPES, nafarelin, norspermidine, nolvadex, NCI NSC-127716, NCI NSC-264880, NCI NSC-39661, NCI NSC-612567, Warner-Lambert PALA, pemetrexed pentostatin, piritrexim, plicamycin, Asahi Chemical PL-AC, raltitrexed stearate; Takeda TAC-788, thioguanine, tiazofurin, Erbamont TIF, trimetrexate, tyrosine kinase inhibitors, tyrosine protein kinase inhibitors, Taiho UFT, toremifene, and uricytin, all of which are disclosed in U.S. Pat. No. 6,916,800, which is herein incorporated by reference in its entirety.

In some embodiments, the antimetabolite agent can be a thymidylate synthase (TS) inhibitor that when administered to a cancer cell of a subject promotes incorporation of a UDG substrate into the DNA of the cell. One example of a thymidylate synthase that is an antimetabolite and induces or promotes incorporation of a UDG substrate, such as uracil, into DNA of cancer cells is 5-fluorouracil (5-FU). 5-Fluorouracil has been used clinically in the treatment of malignant tumors, including, for example, carcinomas, sarcomas, skin cancer, cancer of the digestive organs, and breast cancer. 5-Fluorouracil, however, can cause serious adverse reactions such as nausea, alopecia, diarrhea, stomatitis, leukocytic thrombocytopenia, anorexia, pigmentation, and edema. Derivatives of 5-fluorouracil with anti-cancer activity have been described in U.S. Pat. No. 4,336,381. Further 5-FU derivatives have been described in the following patents listed in JP 50-50383, JP 50-50384, JP 50-64281, JP 51-146482, and JP 53-84981 hereby individually incorporated by reference herein.

In other embodiments, the antimetabolite agent can be an antifolate agent that when administered to a cancer cell of a subject promotes incorporation of a UDG substrate into the DNA of the cell. An example of an antifolate agent is pemetrexed. Pemetrexed inhibits several key folate-dependant enzymes in the thymidine and purine biosynthetic pathways, including thymidylate synthase, dihydrofolate reductase, and glycinamide ribonucleotide formyltransferase. As an analogue of methylenetetrahydrofolate, pemetrexed directly blocks dTMP production by depleting tetrahydrofolate pools required for TS. In comparison to other anti-metabolites, pemetrexed is the most potent inducer of uracil incorporation into DNA.

In still other embodiments, the antimetabolite agent can be a nucleoside analogue that when administered to a cancer cell of a subject promotes incorporation of a UDG substrate into the DNA of the cell. In some examples, the nucleoside analogue can be 2-Fluoroadenosine-5'-phosphate or fludarabine (F-ara-A). Fludarabine is one of the most active agents in the treatment of chronic lymphocytic leukemia. The compound acts by inhibiting DNA synthesis. Treatment of cells with fludarabine is associated with the accumulation of cells at the G1/S phase boundary and in S phase; thus, it is a cell cycle S phase-specific drug. Incorporation of the active metabolite, F-araATP, retards DNA chain elongation. Fludarabine is also a potent inhibitor of ribonucleotide reductase, the key enzyme responsible for the formation of dATP.

Alternatively, an antimetabolite agent can be administered in combination with an AP endonuclease to promote or enhance the cytoxicity of the antimetabolite agent when it is determined that the expression level of UDG for the cancer is higher than the control level. As discussed above, administration to a cancer cell of an antimetabolite in combination with an AP endonuclease inhibitor can enhance antimetabolite induced cell death by binding of the AP endonuclease inhibitor to AP sites that are excised by DNA glycosylases including UDG. This enhances the cytoxicity of the anti-metabolite agents by further inhibition of the BER pathway and allows treatment of cancers that express high levels of UDG that were previously found to be resistant to treatment with antimetabolite agents.

The AP endonuclease inhibitor that potentiates the cytotoxicity of the antimetabolite agent can be a small molecule compound with a primary amine group that forms a covalent linkage with and/or binds to an aldehyde group of an AP site induced by the antimetabolite agent. In single-nucleotide BER, the deoxyribose phosphate (dRP) in the abasic site is removed by the lyase activity of DNA pol β. Binding of the AP endonuclease inhibitor to an aldehyde group can structurally alter the AP site so that AP endonuclease does not recognize the modified AP site and/or prevent AP endonuclease-mediated cleavage of phosphodiester bonds, thus blocking single nucleotide BER.

In some embodiments, the reaction of the AP endonuclease inhibitor with the aldehyde group in the cancer cells can be faster than AP endonuclease to inhibit repair of DNA. Advantageously, administration of the AP endonuclease inhibitor in combination with the antimetabolite agent and/or UDG inhibitor to tumor cells can bypass other resistance factors, such as MMR defects and high MGMT activity in the tumor cells.

In some embodiments, the AP endonuclease inhibitor can be an aminooxy small molecule that can react with an AP site faster than AP endonuclease. One example of an aminooxy compound that that can react with an AP site faster than AP endonuclease is methoxyamine (MX) or salts thereof. Methoxyamine when administered in combination with an antimetabolite agent, such as pemetrexed, to a subject with cancer can potentiate the anticancer effect of the antimetabolite agent without additive systemic toxicity.

In other embodiments the AP endonuclease inhibitor can be a small molecule having the formula V:

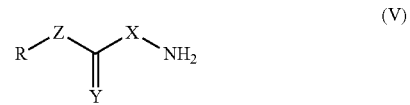

(V)

wherein X is O or NH,

Y is O, S, or NH,

Z is absent or represents O, S, or NH,

R represents a hydrogen or a hydrocarbon moiety, and pharmaceutically acceptable salts thereof.

Other examples of small molecules primary amine compounds that can bind to AP sites and prevent APE-mediated cleavage of phosphodiester bonds include O-benzylhydroxylamine; ethyl aminooxyacetate; aminooxyacetic acid; ethyl aminooxyacetate; $H_2N$—$OCHMeCO_2H$; carboxy- methoxyamine; aminooxyacetic acid; $HN$=$C(NH_2)SCH_2CH_2ONH_2$; $H_2N$—$O(CH_2)_3SC(NH_2)$=$NH$; $MeOC(O)CH(NH_2)CH_2O$—$NH_2$; $H_2NOCH_2CH(NH_2)CO_2H$; canaline; $H_2N$—$O(CH_2)_4O$—$NH_2$; O-(p-nitrobenzyl)hydroxylamine; 2-amino-4-(aminooxymethyl)thiazole; 4-(aminooxymethyl)thiazole; O,O'-(o-phenylenedimethylene)dihydroxylamine; 2,4-dinitrophenoxyamine; O,O'-(m-phenylenedimethylene)dihydroxylamine; O,O'-(p-phenylenedimethylene)dihydroxylamine; $H_2C$=$CHCH_2O$—$NH_2$; $H_2N$—$O(CH_2)_4O$—$NH_2$; $H_3C(CH_2)_{15}O$—$NH_2$, 2,2'-(1,2-ethanediyl)bis(3-aminooxy)butenedioic acid dimethyl diethyl ester; compounds having any of the following structures:

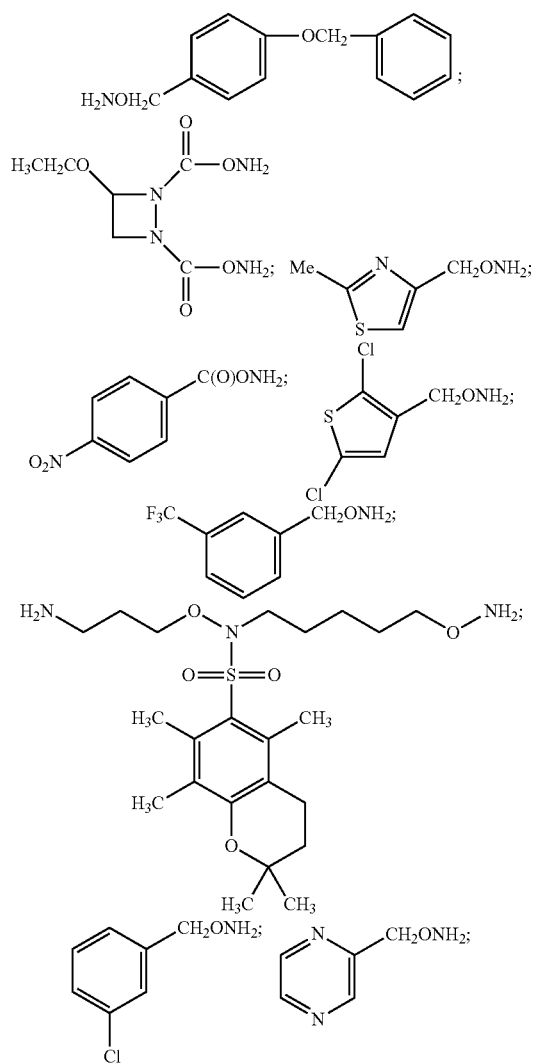

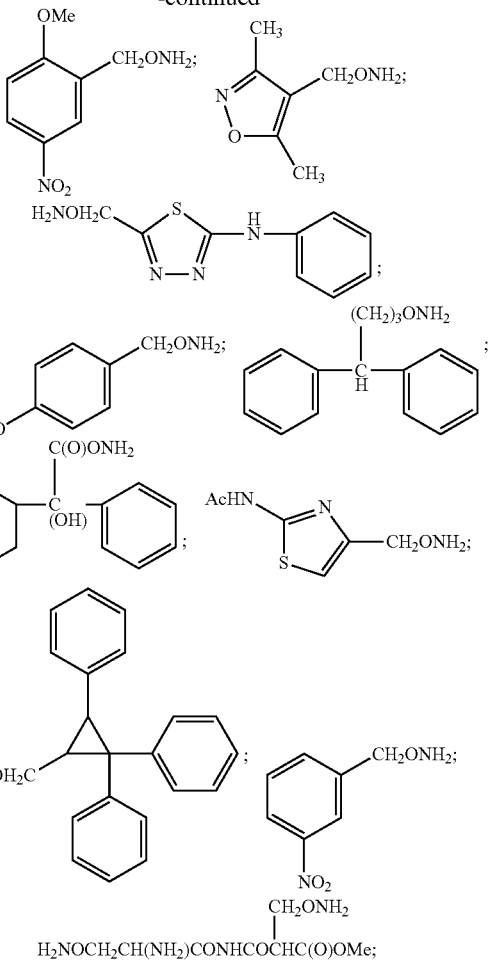

and pharmaceutically acceptable salts of any of these compounds.

Still other examples of small molecules primary amine compounds that can bind to AP sites and prevent APE-mediated cleavage of phosphodiester bonds can be identified using a high-throughput screening assay described in U.S. Pat. Nos. 8,367,332, 8,324,282, 6,635,677, and 6,465,448.

In some embodiments, the antimetabolite agent can be administered to an individual in combination with the AP endonuclease inhibitor. For example, the antimetabolite agent and AP endonuclease inhibitor can be administered to an individual together in a parenteral formulation. Alternatively, the antimetabolite agent and AP endonuclease inhibitor can be administered to an individual together in an oral formulation, such as a solid dosage formulation.

In some embodiments, the antimetabolite agent and AP endonuclease inhibitor can be administered to an individual sequentially, where the individual is first given the antimetabolite agent and then given the AP endonuclease inhibitor. For example, the individual can be given the antimetabolite agent in a parenteral formulation, such as an intravenous formulation, or an oral formulation, such as a solid dosage formulation and then given the AP endonuclease inhibitor in a parenteral formulation, such as an intravenous formulation, or an oral formulation, such as a solid dosage formulation.

Alternatively, in some embodiments, the antimetabolite agent and AP endonuclease inhibitor can be administered to an individual sequentially, where the individual is first given the AP endonuclease inhibitor and then given the antimetabolite agent. For example, the individual can be given the AP endonuclease inhibitor in a parenteral formulation, such as an intravenous formulation, or an oral formulation, such as a solid dosage formulation and then given the antimetabolite agent in a parenteral formulation, such as an intravenous formulation, or an oral formulation, such as a solid dosage formulation.

In some embodiments, the antimetabolite agent and the AP endonuclease inhibitor can create an anticancer effect greater than that of the separate anticancer effects of the individual agents. For example, the combined anticancer effect of the antimetabolite agent and the AP endonuclease inhibitor can be greater than the added anticancer effect of the antimetabolite agent and AP endonuclease inhibitor when used individually.

In certain embodiments, an antimetabolite agent, such as pemetrexed, that induces incorporation of uracil into DNA of the cancer can be administered in combination with an AP endonuclease inhibitor, such as methoxyamine after it is determined that cancer of subject has an increased level of UDG expression compared to a control level.

In some embodiments, the antimetabolite agent can be administered in a dose of from about 10 mg/m$^2$ to about 5,000 mg/m$^2$ body surface area. For example, the dose can be from about 20 mg/m$^2$ to about 200 mg/m$^2$ body surface area; the dose can be from about 150 mg/m$^2$ to about 500 mg/m$^2$ body surface area; the dose can be from about 400 mg/m$^2$ to about 1000 mg/m$^2$ body surface area; the dose can be from about 900 mg/m$^2$ to about 5,000 mg/m$^2$ body surface area; the dose can be from about 200 mg/m$^2$ to about 1,000 mg/m$^2$ body surface area; or the dose can be from about 500 mg/m$^2$ to about 600 mg/m$^2$ body surface area. In some embodiments, the antimetabolite agent can be pemetrexed and pharmaceutically acceptable salts thereof.

In some embodiments, the ratio of AP endonuclease inhibitor to antimetabolite agent can be from about 1 to about 1:10000. For example, ratio of AP endonuclease inhibitor to antimetabolite agent can be from about 1:2 to about 1:100; the ratio of AP endonuclease inhibitor to antimetabolite agent can be from about 1:50 to about 1:500; the ratio of AP endonuclease inhibitor to antimetabolite agent can be from about 1:450 to about 1:10000; the ratio of AP endonuclease inhibitor to antimetabolite agent can be from about 1:5 to about 1:500; the ratio of AP endonuclease inhibitor to antimetabolite agent can be from about 1:10 to about 1:50; the ratio of AP endonuclease inhibitor to antimetabolite agent can be from about 1:15 to about 1:40; or the ratio of AP endonuclease inhibitor to antimetabolite agent can be from about 1:20 to about 1:30.

In some embodiments, an AP endonuclease inhibitor is administered in an amount efficient to enhance or increase the effect of an antimetabolite agent.

In other embodiments, the antimetabolite agent or combination of antimetabolite agent and AP endonuclease inhibitor can be administered to subject in combination with at least one other BER inhibitor. The at least one other BER inhibitor can include, for example, a PARP inhibitor. Examples of PARP inhibitors are 4-amino-1,8-naphthalimide (ANI), PD128763, 3-AB, 6-AN, and 8-hydroxy-2-methyl-quinazolin-4-[$^3$H]one (NU-1025).

Other examples of BER inhibitors that can be administered to the subject in combination with the antimetabolite agent and or AP endonuclease inhibitor include DNA polymerase inhibitors (e.g., DNA polymerase β, γ or ε), such as prunasin, aphidicolin, 2',3'-dideoxycytidine triphosphate (ddCTP), 2',3'-dideoxythymidine triphosphate (ddTTP), 2',3'-dideoxyadenosine triphosphate (ddATP), 2',3'-dideoxyguanosine triphosphate (ddGTP), 1-beta-D-arabinofuranosylcytosine (Ara-C), caffeine, arabinocytidine, and bleomycin.

Still other examples of BER inhibitors include DNA ligase inhibitors (e.g., DNA ligase I, II, or III), such as ursolic and oleanolic acids, aleuritolic acid, protolichesterinic acid, swertifrancheside, fulvoplumierin, fagaronine chloride, and bleomycin. XRCC1 is the protein partner of DNA ligase III, and inhibitors of XRCC1, such as 3-AB, are useful as BER inhibitors as well.

Further examples of BER inhibitors include topoisomerase II inhibitors. Topoisomerase inhibitors induce DNA cleavage and other chromosomal aberrations, including sister chromatid exchanges. Compounds useful as BER inhibitors also include topoisomerase II inhibitors, such as etoposide (VP-16, VP-16-123), meso-4,4'-(2,3-butanediyl)-bis-(2,6-piperazinedione) (ICRF-193, a bisdioxopiperazine), doxorubicin (DOX), L amsacrine (4',9-acridinylaminomethanesulfon-m-anisidide; mAMSA), pazelliptine, nalidixic acid, oxolinic acid, novobiocin, coumermycin A1, fostriecin, teniposide, mitoxantrone, daunorubicin, N-[2-dimethylamino)ethyl]acridine-4-carboxamide (DACA), merbarone, quinacrine, ellipticines, epipodophyllotoxins, ethidium bromide, epirubicin, pirarubicin, 3'-deamino-3'-morpholino-13-deoxo-10-hydroxy caminomycin; 2",3"-bis pentafluorophenoxyacetyl-4',6'-ethylidene-beta-D glucoside of 4'-phosphate-4'-dimethylepipodophyollotoxin 2N-methyl glucamine salt (F11782; a fluorinated lipophilic epipodophylloid), adriamycin, actinomycin D, anthracyclines (such as 9-aminoanthracycline), and pyrazoloacridine (PZA). Topoisomerase I inhibitors, such as camptothecin and topotecan can also be used as BER inhibitors.

In some embodiments, other enzyme inhibitors, whether known in the art or hereafter identified, as well as inhibitors of other elements of the BER pathway, such as DNA alkyltransferase, may be employed in compositions and methods without departing from the scope and spirit of the present embodiments.

In still other embodiments, the antimetabolite agent or combination of antimetabolite agent and AP endonuclease inhibitor can be administered to subject in combination with at least one other anticancer agent that induces formation of AP sites. Anticancer agents that induce the formation of AP sites include intercalating agents, such as bleomycin, adriamycin, quinacrine, echinomycin (a quinoxaline antibiotic), and anthrapyrazoles.

Radiation, such as gamma radiation, UVA, and UVB, can be used to generate AP sites. Ultraviolet light is absorbed in DNA with the formation of UV-specific di-pyrimidine photoproducts. Exposure to gamma irradiation, UVA, and UVB can induce damaged pyrimidine photodimers Anticancer agents that induce the formation of AP sites can also include DNA oxidizing agents, such as hydrogen peroxide.

Anticancer agents that induce the formation of AP sites can further include alkylating agents, such as temozolomide (TMZ),1,3-bis(2-chloroethyl)-1-nitrosourea (BCNU), MeOSO$_2$(CH$_2$)$_2$-lexitropsin (Me-Lex), cis-diamminedichloroplatinum II (cisplat; cis-DDP), mitomycin bioreductive alkylating agents, quinones, streptozotocin, cyclophosphamide, nitrogen mustard family members such as chlorambucil, pentostatin (and related purine analogs), fludarabine, bendamustine hydrochloride, chloroethylating nitrosoureas (e.g., lomustine, fotemustine, cystemustine), dacarbazine (DTIC), and procarbazine. In certain embodiments, the alkylating agent is a nitrosoruea, such as a mustine.

Alkylating agents can function by adding methyl groups to DNA, cross-linking macromolecules essential for cell division, and linking guanine bases in DNA through their $N^7$ atoms. Both inter- and intra-strand cross-links can be mediated by alkylating agents. Inter-strand cross-links prevent the separation of the DNA strands necessary for cell division, and by being more difficult to repair, constitute the more lethal lesion.

In certain embodiments, the anticancer agent is selected from radiosensitizers such as 5-iodo-2'-deoxyuridine (IUdR),6-thioguanine, hypoxanthine, uracil, ecteinascidin-743, and camptothecin and analogs thereof.

In certain embodiments, the anticancer agent is not temozolomide. In certain embodiments, the anticancer agent is not BCNU. In certain embodiments, the anticancer agent is not PE128723, 6-AN, 3-AB, BCNU, or temozolomide It will be appreciated that compositions or formulations provided herein may be in any form, which allows for the composition to be administered to a patient. For example, the composition may be in the form of a solid, liquid or gas (e.g., aerosol). Other routes of administration include, without limitation, oral, topical, parenteral (e.g., sublingually or buccally), sublingual, rectal, vaginal, and intranasal. The term parenteral as used herein includes subcutaneous injections, intravenous, intramuscular, intrasternal, intracavemous, intrathecal, intrameatal, intraurethral injection or infusion techniques. The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

Pharmaceutical compositions can include physiologically acceptable surface active agents, carriers, diluents, excipients, smoothing agents, suspension agents, film forming substances, and coating assistants, or a combination thereof; and a compound disclosed herein. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example, dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compounds can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries, which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Additional therapeutic or diagnostic agents may be incorporated into the pharmaceutical compositions. Alternatively or additionally, pharmaceutical compositions may be combined with other compositions that contain other therapeutic or diagnostic agents.

The compounds or pharmaceutical compositions may be administered to the patient by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; as well as (e) administration topically; as deemed appropriate by those of skill in the art for bringing the compound of the invention into contact with living tissue.

Pharmaceutical compositions suitable for administration include compositions where the active ingredients are contained in an amount effective to achieve its intended purpose. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired effects and the therapeutic indication. Typically, dosages may be between about 10 microgram/kg and 100 mg/kg body weight, preferably between about 100 microgram/kg and 10 mg/kg body weight. Alternatively, dosages may be based and calculated upon the surface area of the patient, as understood by those of skill in the art.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, the present invention will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body weight, and response of the individual patient. A program comparable to that discussed above may be used in veterinary medicine.

Example 1

In this Example, we investigated the impact of UDG and BER on cell sensitivity to pemetrexed using isogenic UDG-proficient and -deficient human cancer cells. Although pemetrexed has multiple targets, the different responses to pemetrexed in $UDG^{+/+}$ and $UDG^{-/-}$ cells were investigated only with respect to the levels of uracil-DNA produced by pemetrexed. We also explored the inhibition of BER by MX as a novel strategy to enhance the therapeutic efficacy of pemetrexed, although MX is expected to potentiate other anticancer agents capable of inducing uracil incorporation into DNA.

Materials and Methods

Cells and Reagents

Stable and complete knockdown of UDG expression in DLD1 colon cancer cells ($DLD1/UDG^{-/-}$ cells) was achieved by homologous recombination, as described by Zhang et al. Briefly, homologous recombination resulted in insertion of a DNA construct containing a series of stop codons within Exon 1 of the UNG gene to interrupt transcription of both the mitochondrial and nuclear UNG isoforms. Recombinant virus was grown in 293T cells and subsequently used to infect DLD1 cells. Selection of positively transfected clones was achieved by the addition of G418 to the culture medium. A second infection of transfected clones with Cre-recombinase adenovirus caused excision of the neomycin resistance cassette. Dflag cell line was produced by transfection of UDG expression vector in $UDG^{-/-}$ cells to restore UDG activity.

Pemetrexed was obtained from LC Laboratories (Woburn, Mass.), 5-Fluorouracil and cisplatin were purchased from Sigma Aldrich (St. Louis, Mo.) and temozolomide was purchased from Ochem Inc (Des Plaines, Ill.). Uracil DNA glycosylase was purchased from New England Biolabs (Ipswich, Mass.) and APE1 was purchased from Trevigen (Gaitherburg, Md.). Methoxyamine (MX), uracil, and uracil-1,3-$^{15}N_2$ were purchased from Sigma Chemical Co (St. Louis, Mo.). MX was dissolved in sterilized water (pH 7.0) at a stock solution of 2.5 M and stored at −20° C. Working solutions were generated prior to experimental use. Fluorescent dye-labeled 40-mer oligonucleotides containing U:G mispairs were purchased from Operon Biotechnologies (Huntsville, Ala.).

Colony Survival Assay

Tumor cells (500-2000/dish) were plated and treated with pemetrexed (0-400 nM), 5-fluorouracil (0-20 μM), temozolomide (0-1500 μM), or cisplatin (0-40 μM). After 7 days, surviving colonies were stained with methylene blue for 30 min at room temperature and the colonies containing more than 50 cells were counted to generate survival curves.

Glycosylase Activity Assay

UDG activity (purified protein or whole cell extracts) was measured using an oligodeoxynucleotide containing a single uracil.

```
5'[HEX]GTAAAACGACGGCCAGTGUATTCGAGCTCGGTACCCGGGG 3'
   CATTTTGCTGCCGGTCACGGAAGCTCGAGCCATGGGCCCC[Cy5].
```

The fluorescent dye-labeled duplex oligonucleotides were incubated with purified UDG at 37° C. for 30 min, followed by 30 min incubation with APE1 or with whole cell extract. The reaction was stopped by incubation at 95° C. for 5 min. Reaction products, 18-mer fragments, were resolved by electrophoresis on denaturing 20% polyacrylamide gels (7 M urea, 1× Trisborate-EDTA). Visualization and quantitation was achieved using a Typhoon 9200 fluorescence Imager (Amersham BioScience, Piscarawat, N.J.). UDG activity was determined based on fluorescence density quantified using ImageQuant software.

AP Site Assay

The number of AP sites was measured using ARP (aldehyde reactive probe) reagent. The assay was performed as previously described. Briefly, cells ($2\times10^6$) were collected after drug treatment and DNA was extracted. DNA (10 μg) was incubated with 15 μl of 1 mM ARP (Dojindo Laboratories, Kumamoto, Japan), and then precipitated and washed with ice-cold ethanol. The ARP-labeled DNA was then heat-denatured at 100° C. for 5 min, quickly chilled on ice and mixed with an equal volume of 2 M ammonium acetate. The DNA was then immobilized on a BA-S 85 nitrocellulose membrane (Schleicher and Schuell, Dassel, Germany) using a minifold II vacuum filter device (Schleicher and Schuell, Dassel, Germany). The membrane was incubated with 0.25% BSA-PBS containing streptavidin-conjugated horseradish peroxidase (BioGenex, SanRamon, Calif.) at room temperature for 40 min with gentle shaking. ARP-labeled AP sites were visualized by chemiluminescence (Amersham Corp, Piscataway, N.J.) followed by quantitative densitometry using NIH Image J software.

Detection and Quantification of Uracil Using HPLC/MS/MS Analysis $UDG^{-/-}$ and $UDG^{+/+}$ cells were exposed to pemetrexed (10 μM) or 5-fluorouracil (10 μM) for 6, 24, 48 and 72 hrs. At indicated time points, cells were harvested and genomic DNA was extracted by phenol/chloroform. Forty μg of DNA were incubated with 10 U of purified UDG (New England Biolabs) in 60 μL of reaction buffer at 37° C. for 2 hrs. The reaction products were dried at 35° C. in a Turbovap under a stream of nitrogen and reconstituted in 150 μL 90% acetonitrile. The analyte was retained by an Atlantis Hilis Silica analytical column (2.1×100 mm, 3.5 μM) and eluted isocratically by a mixture of 90% acetonitrile and 10% 2.0 mM ammonium formate at a flow rate of 0.2 ml/min. The detection was done by an API 3200 MS/MS mass spectrometer.

Immunofluorescence Microscopy

Cells were grown on coverslips and were treated with drugs for 6-24 hrs. Then cells were fixed in 2% paraformaldehyde and permeabilized with 0.2% Triton X-100. Cells were incubated with primary UDG (Abcam, Cambridge, Mass.) or γH2AX (Bethyl, Montgomery, Tex.) antibody for 1 hr at room temperature, followed by incubation with a secondary antibody conjugated with Alexa 488 (green) (Molecular Probes, Carlsband, Calif.). The nucleus was stained using Hoechst 33258 for 15 min at room temperature. Images were digitally captured using an Olympus microscope equipped with a digital camera.

Western Blot Analysis

Cellular protein was quantified spectrophotometrically using the Bio-Rad assay. Equal amounts of proteins (30 μg) were separated by SDS-PAGE and transferred to PVDF membrane (Millipore Cor., Bedford, Mass.). The membrane was incubated with primary antibody in 1% non-fat dry milk solution overnight at 4° C. and followed by the incubation with HRP-conjugated secondary antibody at room temperature for 1 hr. The proteins were visualized by ECL (Amersham Corp, Piscataway, N.J.) according to the manufacturer's instructions. Sources of primary antibody were as follows: cleaved PARP (BD Pharmingen, San Jose, Calif.), γH2AX (Bethyl, Montgomery, Tex.), pChk1, Chk1, pcdc2, cyclin B1, topoisomerase IIα, topoisomerase I, Bax and Bcl2 (Cell Signaling, Danvers, Mass.), phosphor-histone H3 (Upstate Biotechnologies, Bilerica, Mass.) and α-Tubulin (Sigma-Aldrich, St Louis, Mo.).

Cell Cycle Analysis

For cell cycle analysis, $10^6$ cells ($DLD1/UDG^{+/+}$ and $DLD1/UDG^{-/-}$) were plated in 100-mm tissue culture dishes and exposed to pemetrexed (25 nM). After 6, 24 and 72 h of culture, cells were fixed with 80% methanol and washed with ice-cold 1% BSA/PBS. DNA was stained with 20 μg/mL propidium iodide (Sigma-Aldrich) and 2.5 μg/mL of DNase-free RNase A (Roche). The DNA fluorescence of propidium iodide-stained cells was measured with an Elite ESP flow cytometer/cell sorter (Coulter, Miami, Fla.).

Immunofluorescence Microscopy of Replication Foci Stained with CldU and IdU

DNA replication sites were visualized by incorporation of chlorodeoxyuridine (CldU) and iododeoxyuridine (IdU) into DNA. $UDG^{-/-}$ and $UDG^{+/+}$ cells were labeled with 100 μM CldU (ICN, Irvine, Calif.) or IdU (Sigma Chemical Co., St. Louis, Mo.) for 45 min at different time intervals. Cells were washed with PBS, fixed with cold 70% ethanol, and stored at 4° C. For antibody staining, the ethanol was removed, and 100% methanol was added for 5 min. Cells were washed twice with PBS and incubated with 1.5 M HCl for 30 min to denature the DNA. Cells were washed with PBS, permeabilized with 0.5% Tween 20 in PBS for 5 min, and then incubated in 5% BSA (Sigma Chemical Co.) and in PBS for 20 min to reduce nonspecific binding. Primary antibodies CldU (rat anti-BrdU; Accurate Chemical and Science Co., Westbury, N.Y.) and IdU (mouse anti-BrdU; BD Biosciences) were diluted in 1% BSA buffer, added to the slides, and incubated in a humid environment for 2 hrs. Slides were washed with PBS-Tween 20 and then in a high-salt buffer (200 mM NaCl, 0.2% Tween 20, and 0.2% NP-40 in PBS) for 15 min. The samples were incubated with secondary antibodies for 1 h. Finally, slides were washed with PBSTween 20, mounted with Vectashield antifade mounting medium (Vector Laboratories, Inc., Burlingame, Calif.), and stored at 4° C. Images were visualized on a Nikon Eclipse TE-300 confocal microscope. Fluorescence density of CldU or IdU was quantified by NIH image J software.

Xenograft Tumors in Nude Mice

H460 or A549 tumor cells ($5\times10^6$) were injected into bilateral flanks of female athymic NCr (nu/nu) mice (6 weeks old). When the tumor volumes reached 100-150 mm3, mice were divided into control and treatment groups (6-9 mice/group). Nude mice carrying tumors were treated with pemetrexed (150 mg/kg) alone, MX (4 mg/kg) alone or the combination of the two agents, by daily intraperitoneal injection (i.p.) for 5 consecutive days. Tumor measurements were taken every 2 days. Tumor responses were quantified by tumor volume.

Results

UDG Activity Determines the Level of Uracil Retained in DNA

To correlate UDG activity with the cytotoxicity of pemetrexed, comparative studies were performed in UDG$^{+/+}$ and UDG$^{-/-}$ cells. We first confirmed the UDG activity in these cells using an in vitro glycosylase cleavage assay, in which oligonucleotide substrates containing uridine were incubated with either purified UDG/APE1 enzymes or cell extracts. As shown in FIG. 1A, after the reaction with fluorescent probe-labelled oligonucleotide substrates (40-mer) containing U:G mispairs, both purified UDG/APE1 enzymes and cell extracts from UDG$^{+/+}$ cells produced cleaved DNA fragments as an 18-mer band, which resulted from the removal of uracil bases by UDG and subsequent incision of the resultant AP sites by APE1. By contrast, no cleaved fragments were observed in UDG$^{-/-}$ cell extracts after incubation with an even higher concentration of cell extracts. Dflag cells were capable of removing uracil bases. Dflag cells were derived from UDG$^{-/-}$ cells in which UDG activity was restored.

We next determined the levels of uracil in the DNA of UDG$^{+/+}$ and UDG$^{-/-}$ cells following pemetrexed exposure using HPLC/MS/MS. There was an inverse relationship between UDG activity and the level of uracil bases in the DNA (FIG. 1B). A significant amount of uracil was detected in UDG$^{-/-}$ cells, which correlated with the duration of pemetrexed exposure. By contrast, the detectable uracil in the DNA was very low in UDG$^{+/+}$ cells, suggesting that UDG-proficient cells rapidly and efficiently remove the incorporated uracil. We also examined the levels of uracil bases in DNA following treatment with 5-fluorouracil (5-FU), a well-known TS inhibitor capable of introducing uracil into DNA through imbalanced nucleotide pools. Similarly, 5-FU induced greater retention of uracil in UDG$^{-/-}$ cells than in UDG$^{+/+}$ cells (FIG. 1C).

During the BER process, the formation of AP sites in DNA depends on the activity of DNA glycosylases to remove abnormal bases from the DNA. Therefore, the levels of AP sites formed by pemetrexed should be proportional to the cellular activity of UDG and are a surrogate marker for UDG activity in the cells. As shown in FIG. 1D, a dose-dependent formation of AP sites in DNA was detected in UDG$^{+/+}$ but not UDG$^{-/-}$ cells. The lack of detectable AP sites in UDG$^{-/-}$ cells is presumably due to the absence of UDG activity to remove uracil, resulting in the accumulation of uracil bases in the DNA. To confirm this, pemetrexed-induced AP sites in UDG$^{-/-}$ DNA were analysed after incubation with purified UDG enzymes in vitro. As shown in FIG. 1E, increased AP sites were detected as a function of pemetrexed doses.

UDG Activity Determines Cell Sensitivity to Pemetrexed

To determine the correlation between the expression of UDG and the sensitivity to pemetrexed, the cytotoxic effect of pemetrexed was examined in UDG$^{+/+}$ and UDG$^{-/-}$ cells with a clonogenic assay. UDG$^{-/-}$ cells were 10 times more sensitive to pemetrexed than UDG$^{+/+}$ cells (FIG. 2A). The IC$_{50}$ value for pemetrexed was 20 nM in UDG$^{-/-}$ cells, compared to 210 nM in UDG$^{+/+}$ cells. IC$_{50}$ values were interpolated from the dose-response survival curves. The killing effect of pemetrexed in UDG$^{-/-}$ cells was reversed when UDG activity was restored in Dflag cells. Similarly, UDG$^{-/-}$ cells were more sensitive to 5-FU than either UDG$^{+/+}$ or Dflag cells (FIG. 2B). By contrast, no significant differential sensitivity was observed to temozolomide, an alkylating agent, or cisplatin, a crosslinking agent (FIGS. 2C and D), in UDG$^{+/+}$ and UDG$^{-/-}$ cells, suggesting that UDG activity specifically impacts the cytotoxicity of anticancer agents that are capable of inducing the incorporation of uracil bases in DNA.

The Accumulation of Incorporated Uracil in DNA Stalls DNA Replication

To elucidate the underlying mechanisms responsible for pemetrexed's cytotoxicity, we first examined cell cycle progression in response to pemetrexed. As shown in FIG. 3A, pemetrexed (25 nM) caused the arrest of ~25% and 36% of UDG$^{-/-}$ cells in S-phase at 6 and 24 hr, respectively (FIG. 3A). The S-phase arrest lasted more than 72 hr. At this time point, 35% of the cells were still in S-phase and ~22% of the cells had undergone apoptosis (subG1). By contrast, progression of the cell cycle in UDG$^{+/+}$ cells was only slightly affected by this dose of pemetrexed (FIG. 3B). At 24 hr after pemetrexed treatment, 21% of the cells were transiently arrested in S-phase, in comparison with 17% of untreated cells in S-phase; at 72 hr, UDG$^{+/+}$ cells exhibited a normal cell cycle distribution, with only 6% of the cells in the subG1 compartment (FIG. 3b).

We next examined a network of proteins responsible for DNA damage checkpoints following exposure to pemetrexed. We found that phospho-Chk1 (Ser345) was significantly increased in UDG$^{-/-}$ cells (FIG. 3C) but not in UDG$^{+/+}$ cells (FIG. 3D). As a DNA damage checkpoint kinase, Chk1 is indispensable for cell cycle arrest in response to stalled replication forks, and these results suggest that the accumulation of uracil in the DNA of UDG$^{-/-}$ cells blocks DNA replication and arrests cells in S-phase. In addition, cyclin E was remarkably up-regulated 24 hr after exposure to pemetrexed in both UDG$^{-/-}$ and UDG$^{+/+}$ cells. Although the role of cyclin E remains to be fully elucidated, it is known that it is expressed from the late G1 phase of the cell cycle until the end of S-phase. Thus, cyclin E functions as a regulator of S-phase entry. The strong up-regulation of cyclin E suggests that cyclin E is a sensitive molecule in the response to replication stress induced by pemetrexed. Moreover, the alteration of cdc2, cyclin B1, and phospho-histone H3 in both cell lines (FIGS. 3c and d) also indicates that pemetrexed-induced DNA damage activates S- and M-phase checkpoints. In addition, pemetrexed induced an increase in the expression of topoisomerase IIα (topo IIα) that was much greater in UDG$^{-/-}$ cells than in UDG$^{+/+}$ cells. The induction of topo IIα may be associated with either a global signal of DNA damage or a more specific response to S-phase arrest. Interestingly, although checkpoint activation in response to pemetrexed-induced DNA damage was obviously observed in UDG$^{-/-}$ cells, there was no dose-response relationship between pemetrexed treatment and the alteration of the components involved in the checkpoint network. This suggests that lower doses of pemetrexed efficiently kill UDG$^{-/-}$ cells. As expected, un-removed uracil bases in UDG$^{-/-}$ cells induce replication fork collapse and apoptosis, resulting in marked increases in the protein levels of γH2AX (the marker of DNA double strand breaks) and cleaved PARP (a hallmark of apoptotic cell death) in UDG$^{-/-}$ cells (FIGS. 3C and D). However, it is noteworthy that Bcl2 and Bax remained consistent before and after pemetrexed treatment, suggesting that pemetrexedinduced apoptotic cell death may not be mediated through the mitochondrial apoptosis pathway or that other apoptosis regulators are more important in these cells.

We further investigated whether uracil-DNA lesions could inhibit DNA replication. Cells were sequentially labelled with the halogenated nucleotides CldU and IdU to stain replication foci. Representative cells are depicted in FIGS. 4B and C. Compared to replication foci stained with CldU and IdU in untreated cells, a significant reduction in IdU incorporation was observed in UDG$^{-/-}$ cells following a 6 hr exposure to pemetrexed and a further 18 hr post-incubation, suggesting that pemetrexed-induced accumulation of uracil has the potential to inhibit DNA replication. By contrast, there was no significant change in CldU and IdU incorporation in the replication foci of UDG$^{+/+}$ cells before and after pemetrexed treatment (25 nM). The fluorescence density of IdU or CldU was quantified in UDG$^{-/-}$ and UDG$^{+/+}$ cells by using NIH Image J software. The values of the ratio of IdU to CldU for the control, 6-hr, and 18-hr samples (n=10 cells/time point) were 0.9±0.12, 0.1±0.04, and 0.01±0.005 in UDG$^{-/-}$ cells versus 1.1±0.21, 0.7±0.13, and 0.9±0.31 in UDG$^{+/+}$ cells (FIG. 4D). The difference in inhibition of DNA replication in UDG$^{-/-}$ and UDG$^{+/+}$ cells treated with the same concentration of pemetrexed suggests that accumulated uracil bases in DNA block DNA replication in UDG$^{-/-}$ cells.

Blocking BER Enhances Pemetrexed Cytotoxicity

We have shown above that the lack of UDG activity sensitises tumour cells to antimetabolites, such as 5-FU and pemetrexed. UDG is expressed in several types of human tumours at higher levels than in the corresponding normal tissues, including lung cancer. Thus, the removal of uracil by UDG and subsequent BER activity limits the efficacy of pemetrexed in lung cancer treatment.

We next studied a therapeutic strategy to override the UDG-conferred resistance to pemetrexed by interrupting the BER pathway using MX. Cytotoxicity was measured in UDG and UDG$^{-/-}$ cells after treatment with pemetrexed alone or in combination with MX. MX greatly sensitized UDG$^{-/-}$ cells to pemetrexed and reduced the pemetrexed IC50 value from 220 to 80 nM (FIG. 5a). By contrast, no differential sensitivity between pemetrexed alone and pemetrexed in combination with MX was observed in UDG$^{-/-}$ cells (FIG. 5b). The failure of MX to potentiate pemetrexed toxicity in UDG$^{-/-}$ cells can be explained by the fact that, in UDG$^{-/-}$ cells, there are no DNA binding sites available for MX due to the absence of AP sites in the DNA (FIG. 1D). Similar experiments were performed in the human non-small cell lung cancer cell lines H460 and A549 (FIG. 5C, D, E). These two cell lines retain wild-type p53 and harbour a mutation in K-ras but express different levels of UDG. Western blotting revealed that UDG protein levels in A549 were approximately 9- and 17-fold higher than in H460 cells and normal lung epithelial cells, respectively, as quantified by NIH Image J software (FIG. 5D). Interestingly, A549 cells were more resistant to pemetrexed than H460 cells. IC$_{50}$ values for pemetrexed were 1200 nM in A549, compared to 110 nM in H460 cells. MX was capable of enhancing pemetrexed cytotoxicity in both cell lines 4- to 5-fold as determined by the modification ratio (i.e., IC$_{50}$ of pemetrexed alone/IC$_{50}$ of pemetrexed in combination with MX) (FIG. 5E). Thus, although multiple mechanisms may confer resistance to pemetrexed, the results obtained from the lung cancer cell lines confirmed that UDG activity in tumour cells is an important factor in pemetrexed resistance and that MX can reverse this resistance.

AP sites were detected in H460 cells following treatment with pemetrexed. As shown in FIG. 6a, the formation of AP sites increased as the concentration of pemetrexed increased. Cotreatment with MX formed MX-bound AP sites, resulting in the reduction of ARP-detected AP sites. This is because ARP and MX react competitively with the aldehyde group in AP sites and binding of MX to the AP sites makes them unavailable for ARP binding (FIG. 6a). Furthermore, the levels of UDG protein were significantly induced in cells treated with the combination of pemetrexed and MX (FIG. 6b). Immunofluorescent staining revealed that the UDG protein was increased in both the cytosol and the nucleus but predominantly accumulated in the nucleus (FIG. 6c), suggesting that MX-bound AP sites were able to trap or stabilise UDG in DNA. In addition, immunofluorescent staining and western blot analysis demonstrated a concomitant induction of topo IIα, γH2AX and cleaved PARP in response to the combination of pemetrexed and MX (FIGS. 6D and E). These results could be explained by our previous findings that MXbound AP sites were capable of poisoning topo IIα and inducing topo IIα-mediated DNA double strand breaks, triggering apoptosis.

MX Potentiates the Anti-Tumour Effects of Pemetrexed In Vivo

The MX-potentiated antitumour effect of pemetrexed was further tested in vivo using human lung cancer xenografts. As shown in FIG. 7, both H460 and A549 tumours were moderately sensitive to pemetrexed alone. However, the antitumour activity of pemetrexed was significantly enhanced by the combination of pemetrexed (150 mg/kg) and MX (4 mg/kg) in these two xenograft tumours. At 15 days, H460 xenografts treated with PBS (control group) had a mean tumour volume of 2100±106 mm3, compared with a mean tumour volume of 1726±176 mm3 or 543±82 mm3 (*p<0.02) in mice treated with either pemetrexed alone or in combination with MX, respectively. Similar results were observed in A549 lung cancer xenografts. Importantly, at these doses, mice did not present evidence of systemic toxicity as evaluated by body weight measurements and complete blood count tests (data not shown).

Example 2

In Example 1, we showed that DLD1 human colon cancer cells lacking UNG (i.e., UDG) are hypersensitive to pemetrexed-induced uracil accumulation resulting in cell cycle arrest, DNA double strand break (DSB) formation, and apoptosis. Since pemetrexed is primarily used in the treatment of lung cancer and is limited by a response rate of 30-40% with no long-term sustained responses, we evaluated in Example 2 the relationship between UNG expression and pemetrexed response in human lung cancer cell lines. Gene expression data in cell lines and primary human lung tumor tissue samples suggest a spectrum of UNG expression in lung cancer specimen that is significantly correlated with pemetrexed response. Based on evidence of DNA replication fork instability in the context of deficient uracil excision, we propose a novel role for misincorporated uracil as a genotoxic lesion that contributes to antifolate-induced DSB formation and cell death. Induction of UNG in response to acute and chronic pemetrexed exposure also suggests UNG activity limits pemetrexed cytotoxicity. Differential UNG expression among lung cancer histological subtypes shows UNG as a clinical predictive marker for pemetrexed response. The correlation between UNG expression and pemetrexed sensitivity in experimental models justifies targeting UNG to enhance pemetrexed anti-cancer activity NSCLC.

Materials and Methods

Cell Lines and Reagents

Pemetrexed was purchased from LC Laboratories. Thymidine, 5-Fluorouracil, Cisplatin, Methoxyamine-HCL and Raltitrexed were purchased from Sigma Aldrich. Temozolomide was purchased from O-Chem, Inc (Des Plaines, Ill.). All cell lines were obtained from ATCC and expanded upon delivery into numerous vials of low passage cells for cryopreservation. Cells were passaged for no longer than 3 months. Cell line characterization by ATCC is conducted through short tandem repeat (STR) typing. Re-authentication was not conducted. Adherent cells were maintained in complete DMEM (10% FBS, 2 mM L-Glutamine) and suspension cells were maintained in complete RPMI-1640 (10% FBS, 2 mM L-glutamine) at 37° C. in a 5% $CO_2$ incubator.

Cell Cycle Analysis

Propidium iodine (PI) staining of methanol fixed cells was for cell cycle determinations. Where indicated, FITC labeled PCNA antibody (PCNA-FITC, Abcam) was added for PCNA detection. Uni-parameter (PI-only) and dual-parameter (PI+PCNA-FITC) analysis was performed on a Coulter flow cytometer (EPICS-XL-MCL). Cell cycle histograms (PI) and PCNA dot plots (PCNA-FITC) were de-convoluted from ≥20,000 events using FlowJo software.

Western Blot

Protein extracts (25 μg) were resolved by SDS-PAGE and transferred to PVDF membrane (Millipore). Non-specific binding sites were blocked in 5% milk in PBST (1×PBS+ 0.1% Tween-20). Incubation with primary antibody at 4° C. in 5% BSA/PBS was followed by incubation with HRP-conjugated secondary antibody in 2.5% milk in PBST. Proteins were visualized with ECL reagent (Amersham Corp). Chromatinbound proteins were extracted from formaldehyde (1%) cross-linked cells using Pierce Chromatin Prep Module (Thermo Pierce). Antibody sources: UNG-23936 (39 kDa band, nuclear UNG) and PCNA (Abcam); Tubulin (Calbiochem); γH2AX and Histone-H3 (Millipore); Cleaved PARP (Cell Signaling); and p-chk1, chk1, cdc2, and p-cdc2 (Santa Cruz).

UNG Activity Assay

UNG activity was measured using a 40-mer oligodeoxynucleotide duplex: 5' [HEX] GTAAAACGACGGCCAGT-GUCTTCGAGCTCGGTACCCGGGG (top) 3'-CATTTT-GCTGCCGGTCACAGAAGCTCGAGCCATGGGCCCC [Cy5] (bottom). In fluorescent images, the top and bottom strands appear green and red, respectively. Oligonucleotide duplexes were incubated with either purified enzymes (1 unit) or whole cell extract (2.5 μg) at 37° C. for 30 minutes. The reaction was heat-killed at 95° C., reaction products were resolved by electrophoresis on denaturing 20% polyacrylamide gels, and visualized with a Typhoon 9200 fluorescence imager (Amersham Bioscience, Piscataway, N.J., USA). UNG activity (percentage of cutting) was defined as the fluorescence density of the cut band (20-mer) relative to the sum of the fluorescence intensity of the cut (20-mer) and uncut (40-mer) bands using ImageQuant software (Amersham BioScience).

Abasic (AP) Site Detection

Following drug treatment cellular DNA extracts were labeled with a biotinylated aldehyde reactive probe (ARP) for chemiluminescent AP site detection as previously described. (21) For UNG deficient cells, an additional incubation at 37° C. with recombinant UNG (1 U UNG/100 μg DNA) liberated genomic uracil prior to ARP labeling. Quantitative densitometry was performed using Image J software.

Neutral Comet Assay

Treated cells were processed for comet tail formation under neutral comet assay conditions according to the manufacturers instructions for cell lysis and single cell electrophoresis (Trevigen). Tail lengths were recorded for at least 50 comets on two separate slides (~100 cells per treatment) using Image J software.

Colony Survival Assay

For cells in suspension, colony survival was determined by crystal violet staining of colonies formed after 10-day exposure of $5 \times 10^3$ cells to pemetrexed in soft agar. For adherent cells, colony survival was determined by methylene blue staining of colonies formed after 10-day exposure of 100 cells to pemetrexed in 6-well culture dishes. Only colonies containing ≥50 cells were counted. Data points represent percent of colonies relative to untreated control averaged over 3 experiments.

Reverse Transcriptase Polymerase Chain Reaction (qRT-PCR)

Lung cancer cDNA microarray was purchased from Origene. For cell lines, total RNA was extracted from cells using RNAqueous-4PCR kit (Ambion, Austin, Tex.). Random hexamers (Invitrogen) were used to PCR amplify cDNA from 1 μg of RNA extract. TaqMAN MGB probes (FAMTM dye labeled, Applied Biosystems) for nuclear UNG (UNG2), SMUG1, MBD4, TDG, TYMS and βPol amplified cDNA using 40 cycles of PCR in an ABI 7500 Fast Real-Time PCR System (Applied Biosystems, Foster City, Calif.). Target quantification was achieved after normalization to β-actin amplification as an endogenous control and is presented as relative quantification (RQ) values or log-mean RQ values.

siRNA and shRNA Transfection

UNG directed shRNA and siRNA plasmids were purchased from Origene. Transfection was carried out according to manufacturer specifications. Stably transfected clones (shRNA) were selected with puromycin with subsequent expansion of a well-isolated colony of cells.

Pemetrexed-Resistant Cell Lines

H1299 cells were exposed to step-wise increasing concentrations of pemetrexed over a period of 4 months. UNG expression was monitored in the bulk population at 2, 8, 12 and 16 weeks prior to administration of the induction dosage and at 24 weeks in a population of bulk chronically exposed cells that had been without pemetrexed for 8 weeks. H1299 cells capable of growth in 50 nM pemetrexed selection pressure were subcloned by limiting dilution in 96 well plates. Independent sublines were designated H1299/PR-1 and H1299/PR-2.

Xenografts in Nod-Scid Mice

Tumor cells in early passage ($5 \times 10^6$) were injected into bilateral flanks of female NODSCID mice (6 weeks old). When tumor volumes reached 100 mm3, mice were divided into control (n=4) and treatment (n=6) groups. Mice bearing tumors were treated with pemetrexed (150 mg/kg) or 100 μl sterile PBS (control) by daily intraperitoneal injection (IP) for 5 consecutive days. Tumor measurements were taken every 2 days and response was quantified by tumor volume.

Statistical Analysis

Results are presented as the mean±SEM. Significance, assigned for p-values<0.05, was determined by unpaired 2-tailed student's t-test with standard software (GraphPad Prism, San Diego, Calif., USA). Correlations of gene expression with pemetrexed $IC_{50}$ were estimated using Pearson correlation coefficient. Expression of expression UNG and other genes of interest was compared using analysis of variance (ANOVA) followed by Tukey's pair-wise comparison procedure. The effects of multiple genes on drug $IC_{50}$ were estimated using multivariable regression models, i.e. $IC_{50}$=intercept+coefficient1(gene1)+coeficient2(gene2)+ε.

Results

A Spectrum of UNG Expression Exists in Human Lung Cancer

Our previous observation Example 1 of profound pemetrexed sensitivity in UNG−/− colon cancer cells prompted us to investigate the value of UNG as a mechanistic and predictive marker for pemetrexed response in human lung cancer. To do this, we evaluated UNG expression and pemetrexed sensitivity ($IC_{50}$) in a panel of 8 lung cancer cell lines and two non-malignant lung cell lines. UNG protein (FIG. 8a) and transcript (FIG. 8b) levels were significantly higher in lung cancer cell lines compared to non-malignant lung epithelial cells (WI38 and IMR90). Additionally, lung cancer cell lines derived from small cell (H69) and squamous cell (Calu-1) carcinoma, known to be clinically unresponsive to pemetrexed, had higher levels of UNG compared to adenocarcinoma and large cell carcinoma cell lines (FIG. 8a-b). Pemetrexed $IC_{50}$ was determined from colony survival experiments (FIG. 8c). Plotting UNG levels (protein band density, FIG. 8d) or UNG mRNA levels (relative quantification (RQ) value, FIG. 8e) against pemetrexed $IC_{50}$ for each cell line indicated that UNG expression was well correlated with pemetrexed $IC_{50}$ (protein—Pearson r=0.79, p=0.021; mRNA—Pearson r=0.71, p=0.047). Pemetrexed $IC_{50}$ was not significantly correlated with mRNA expression of other BER genes, including other glycosylases with uracil excision activity (SMUG1, TDG, and MBD4), DNA polymerase β (Polβ0) or the pemetrexed target gene, TYMS (FIG. 8f). UNG mRNA levels were still marginally predictive of the pemetrexed $IC_{50}$ (p<0.1) when paired with other pathway specific genes in multivariable regression analysis. Overall, these data illustrate a spectrum of UNG expression in human lung cancer cell lines that is positively correlated with pemetrexed response. Measurement of UNG expression in primary human lung cancer tissue cDNA microarrays evinced significant variation in UNG expression among histological subtypes (FIG. 8g). Similar to cell lines, UNG was elevated in lung cancer compared to non-malignant tissue cDNAs. Additionally, cDNA from small cell and squamous cell carcinoma had significantly higher UNG expression compared to adenocarcinoma (p<0.0001, Tukey's procedure). Pooled analysis of published microarray data corroborated our findings (FIG. 8h). These data also showed that UNG expression was correlated with higher grade adenocarcinoma) and reduced 1-year survival. While clinical response data are unavailable for these samples, higher UNG levels in lung cancer histological subtypes that are reportedly pemetrexed resistant suggest a clinically relevant correlation between UNG expression and pemetrexed response. Thymidylate synthetase (TYMS), which has been associated with pemetrexed resistance, was also differentially expressed among the various lung cancer subtypes in the datasets analyzed. Squamous but not small cell carcinoma TYMS expression was significantly higher than adenocarcinoma (FIG. 8i). We were unable to locate tissue sets from recent pemetrexed clinical trials in lung cancer to interrogate for UNG expression. We have initiated prospective collection of lung cancer tissue samples from patients receiving pemetrexed to directly evaluate the relationship between UNG expression and pemetrexed response.

Loss of UNG Expression Increases Lung Cancer Sensitivity to Pemetrexed

We validated the correlation between UNG expression and pemetrexed response through direct targeting of UNG expression with siRNA and shRNA. For this analysis we used adenocarcinoma cell lines, A549 and H1975, which have moderate and high baseline UNG expression, respectively. Targeting of A549 cells with UNG directed siRNA resulted in 70% reduction of UNG protein expression (FIG. 9a-b). A549 siRNA cells were 7-fold more sensitive to pemetrexed compared to parental cells (A549 siUNG $IC_{50}$=60.54 nM; A549 parental $IC_{50}$=416.1 nM, p<0.0001, FIG. 9c). Similarly, stable transfection of H1975 cells with UNG directed shRNA resulted in 50-60% knockdown of UNG protein expression (FIG. 9d-e). In colony survival assays (FIG. 9f), shRNA targeted H1975 clones were > 5-fold more sensitive to pemetrexed than parental cells ($IC_{50}$ values: H1975=776.6 nM; H1975 66 shUNG=130.9 nM; H1975 67 shUNG=146.2 nM, p<0.0001). UNG deficient H1975 cells displayed some cross sensitivity to raltitrexed and 5-fluorouracil but not temozolomide or cisplatin suggesting the effects of UNG loss are specific to TYMS inhibitors.

To determine the impact of UNG expression on pemetrexed sensitivity in vivo, H1975 and H1975 66 shUNG cells were xenografted subcutaneously into NODSCID mice. Treatment with 5 daily consecutive intraperitoneal (IP) injections of pemetrexed (150 mg/kg) evinced a tumor quadrupling time of 9.68±0.31 days in H1975 wt tumors compared to 13.67±0.28 days for H1975 shUNG tumors. At day 20, pemetrexed treated H1975 66 shUNG tumors were 55.6% smaller than untreated controls while H1975 wild type tumors were only 37.8% smaller than untreated controls, p<0.001 (FIG. 9g). These data indicate a significant increase in the anti-tumor effect of pemetrexed on tumors with lower levels of UNG expression, in vivo.

Limited Uracil Removal is Associated with Increased DNA Damage in UNG Deficient Cells UNG is the major glycosylase responsible for removing uracil that is misincorporated during DNA replication. To relate pemetrexed sensitivity in UNG deficient cells to the retention of uracil in DNA, we first evaluated uracil excision capacity of UNG knockdown cells. UNG knockdown did not alter expression of other glycosylases capable of uracil excision (FIG. 10a). Protein extracts from untreated H1975 66 shUNG cells had diminished capacity to excise uracil from a synthetic oligonucleotide duplex containing a single uracil residue (FIG. 10b-c). In pemetrexedexposed cells, AP site detection was used as a surrogate measure of accumulated uracil. H1975 parental and H1975 66shUNG cells were treated with pemetrexed for 0-48 hours. Following treatment, DNA extracts from treated cells were labeled with chemiluminescent aldehyde reactive probe (ARP) that binds glycosylase-generated AP sites. Compared to control cells, H1975 shUNG cells had decreased AP site detection, p<0.05 (FIG. 10d). Lack of AP site formation following pemetrexed exposure suggests decreased uracil excision and accumulation of uracil bases in DNA. To verify that uracil was retained in the DNA of cells with low UNG expression, we incubated DNA extract of pemetrexed-treated H1975 shUNG cells with recombinant UNG enzyme before labeling with ARP to detect AP sites. This in vitro uracil excision reaction resulted in the chemiluminescent detection of AP sites thereby confirming the persistence of uracil in H1975 shUNG DNA (FIG. 10e).

To determine the mechanisms responsible for enhanced pemetrexed sensitivity in UNG deficient cells, we compared cell cycle progression and expression of DNA damage response proteins in pemetrexed treated UNG competent and UNG knockdown cells. Stable knockdown of UNG (H1975 66 shUNG cells) conferred increased sensitivity to pemetrexed-mediated accumulation of early S-phase and sub-G1 cells (FIG. 11a), despite similar doubling times. S-phase accumulation was accompanied by induction of phospho-cdc2, phospho-chk1, and cyclin B1 (FIG. 11b). H1975 66 shUNG cells also had increased DNA DSB formation, as indicated by increased levels of γ-H2AX (FIG. 11b) and significantly increased comet tail lengths (p<0.0001) in neutral assay conditions (FIG. 11c). H1975 shUNG cells were also more sensitive to pemetrexed induced apoptosis as indicated by increased levels of cleaved poly-ADP ribose polymerase (PARP) (FIG. 11b). These data are consistent with the DNA damage response observed in DLD1 UNG−/− cells treated with pemetrexed and support our prior conclusion that cells lacking UNG are more sensitive to pemetrexed induced cell cycle arrest, DNA DSB formation and apoptosis.

Prolonged S-phase arrest is known to result in DNA DSB formation due to the collapse of stalled replication forks. We evaluated the stability of the DNA replication fork in pemetrexed treated lung cancer cells with native and reduced levels of UNG protein. Nucleotide incorporation experiments using CldU and IdU indicate decreased postpemetrexed treatment nucleotide incorporation (data not shown). However, because CldU and IdU compete with dU for incorporation sites, these data are difficult to interpret prompting us to use an alternative measure of replication stability. Using bi-parametric flow cytometry we measured the dissociation of the replication fork processivity factor, PCNA at the single cell level in H1975 cells expressing UNG directed shRNA. Similar assays have been utilized to detect replication fork disassembly following etoposide and hydroxyurea exposure. PCNA dissociation was determined by the percentage of cells in S phase having low PCNA (red box, FIG. 11d). In wild type cells, less than 1% of cells in treated and untreated samples had low PCNA staining in S phase compared to 3.88±0.93% and 7.81±1.19%, H1975 shUNG cells treated with 25 nM pemetrexed for 6 and 24 hours, respectively, p<0.001 (FIG. 11d). As a complimentary experiment, we examined the expression of chromatin-bound PCNA after pemetrexed treatment by western blot of chromatin cellular extracts. Pemetrexed treatment resulted in reduced expression of chromatin-bound PCNA in shUNG cells (FIG. 11e). Such dispersal of PCNA and other replication fork components from chromatin is indicative of collapsing replication forks and our data implicate pemetrexed-mediated replication fork instability and subsequent fork collapse in the mechanism of DSB formation and cell death observed in pemetrexed-treated UNG deficient cells.

Lastly, to link the accumulation and retention of genomic uracil with pemetrexed cytotoxicity, we used supplemental thymidine to promote salvage pathway production of dTMPs (FIG. 11f). In H1975 cells treated with varying concentrations of pemetrexed alone or in the presence of 10 μM supplemental thymidine, the addition of thymidine rescued pemetrexed sensitivity in H1975 shUNG cells (FIG. 11g). Supplemental thymidine also significantly decreased pemetrexed-mediated induction of γ-H2AX (FIG. 11h). Importantly, AP site detection in H1975 parental cells and in H1975 shUNG DNA extracts incubated in vitro with purified UNG was also limited by the addition of thymidine. Reduced UNG excision (fewer AP sites) suggests supplemental thymidine dampens genomic uracil misincorporation. These data support the hypothesis that pemetrexed-induced cell cycle arrest and DSB formation are consequences of uracil misincorporation.

UNG is Induced in Response to Acute and Chronic Pemetrexed Exposure

Resistance to anti-cancer agents that induce DNA damage has long been associated with up-regulation of DNA repair genes. Pemetrexed resistance in cells with high UNG expression led us to hypothesize that UNG, by limiting uracil-DNA, promotes survival of pemetrexed exposed cells. We assessed the impact of acute and chronic pemetrexed exposure on lung cancer cell expression of UNG. Acute pemetrexed exposure in the pemetrexed-sensitive adenocarcinoma cell line, H460 revealed time- and dosedependent induction of UNG protein and transcript (FIG. 12a-d). Supplemental thymidine dampened the UNG induction response, linking the observation of UNG induction to TYMS inhibition and consequent uracil accumulation (FIG. 12e).

To investigate whether chronic pemetrexed exposure would select for cells with elevated UNG expression, we established pemetrexed resistant sublines. We chose to induce resistance in H1299 cells (adenocarcinoma), the most pemetrexed sensitive cell line in our panel, which also expressed low levels of UNG. Sequential exposure of H1299 parental cells to increasing concentrations of pemetrexed over a 16-week period resulted in chronically elevated UNG protein expression that persisted for 8 weeks when pemetrexed was withdrawn (FIG. 13a). Clonogenic sublines, PR-1 and PR-2, were established and colony survival revealed 25-fold and 71-fold relative resistance to pemetrexed compared to parental cells, p<0.0001 (FIG. 13b). Western blot analysis confirmed induction of UNG in PR1 and PR2 (FIG. 13c). UNG activity was also enhanced, as indicated by UNG cutting assay (FIG. 13d-e) and increased AP site detection in DNA extracts from pemetrexed treated pemetrexed resistant sublines (FIG. 13f). PR-1 and PR-2 cells displayed cross-resistance to the TYMS inhibitors raltitrexed and 5-fluorouracil but were not resistant to other DNA damaging chemotherapeutics such as cisplatin or temozolomide that are not known to induce DNA repair through UNG initiated-BER. Transfection of UNG-directed siRNA into PR-1 cells restored pemetrexed sensitivity (FIG. 13g), indicating that UNG expression contributes significantly to the development of acquired pemetrexed resistance. The acute and chronic induction of UNG protein in lung cancer cells exposed to pemetrexed suggests that UNG activity is a pro-survival response to pemetrexed induced uracil incorporation into DNA and the resulting DNA damage.

Increased BER gene expression and activity prompted us to investigate BER inhibition as a means to re-sensitize chronically exposed cells to pemetrexed. The BER inhibitor methoxyamine (MX) covalently binds the aldehyde of glycosylase-formed AP sites and blocks downstream BER. This agent is now in phase I clinical trials. Recent data has documented in-human tolerance and potential efficacy when combined with pemetrexed. Because MX is well tolerated at 3 mM in cell culture and does not impact cellular sensitivity to non-AP site producing chemotherapeutics, we have surmised that the potentiation of cytotoxicity is due primarily to MX interaction with AP sites versus non-specific interactions with other intracellular aldehydes. MX-bound AP sites are substrates for topoisomerase IIa (TOPOIIα) cleavage and DNA DSB formation. Cells with elevated TOPOIIα are more sensitive to MX potentiation of DNA damaging agent cytotoxicity. Interestingly, TOPOIIα expression is elevated in pemetrexed resistant histological subtypes of lung cancer primary tissues compared to adenocarcinoma, and we observed up-regulation of TOPOIIα in both pemetrexed resistant H1299 subclones compared to parental cells. Potentiation of pemetrexed cytotoxicity by MX is attenuated in UNG deficient cells suggesting that MX effects are critically linked to UNG expression and activity. In colony survival experiments, 3 mM MX co-treatment restored cellular sensitivity to pemetrexed in PR-1 cells (FIG. 13h) further suggesting that pemetrexed response is critically linked to uracil excision by UNG, and in doing so highlighting the utility of BER blockade to override acquired pemetrexed resistance.

This Example shows a significant role for UNG directed BER as a determinant of pemetrexed sensitivity in lung cancer. We observe a spectrum of UNG expression in human lung cancer that is well correlated with pemetrexed $IC_{50}$ in cell lines and trends higher in pemetrexed-resistant small and squamous cell lung cancer subtypes. UNG has been identified as a prognostic marker in NSCLC. Among lung adenocarcinoma tissues, relationships between elevated high UNG expression and both decreased survival and advanced disease stage were noted.

Other DNA glycosylases were not significantly associated with pemetrexed sensitivity and did not compensate for UNG loss suggesting UNG is the major glycosylase for uracil removal in pemetrexed-treated cells. The correlation between UNG expression and pemetrexed $IC_{50}$ remained marginally significant in multivariable regression models controlling for the expression of other BER genes and TYMS, with slight improvements in coefficients of determination.

Prolonged cellular exposure to TYMS inhibitors results in growth arrest or resistance and patients receiving pemetrexed ultimately progress. Continued clinical success of pemetrexed and other TYMS inhibitor chemotherapeutics therefore depends upon biomarker-based patient selection. Thymidylate synthetase (TYMS) levels have been studied for predictive value in pemetrexed sensitivity. Increased intra-tumor levels of TYMS—observed in highly proliferating tumors—limit dTTP pool depletion and contribute to TYMS inhibitor resistance. Additionally, in lung cancer models of acquired pemetrexed resistance, TYMS is consistently elevated. Significant correlation between expression of TYMS and pemetrexed $IC_{50}$ in NSCLC cell lines and a modest survival advantage in patients have also been reported. High TYMS expression has been reported in high-grade small cell carcinoma (SCLC). However, TYMS has failed to predict SCLC response to pemetrexed combination therapy and recent data suggests TYMS has less predictive value beyond second line therapy. In our analysis, TYMS was significantly elevated in cell lines (PR1 and PR2) with acquired pemetrexed resistance. We did not, however, observe significant correlation between pemetrexed $IC_{50}$ and TYMS expression in our panel of cell lines.

Like TYMS, UNG expression is correlated with cellular proliferation. UNG-initiated BER has been observed at replication foci, illustrating coordination of DNA replication and repair of uracil-DNA. Despite observations of high UNG expression in rapidly proliferating cells, neither loss of UNG nor chronic pemetrexed exposure altered cellular doubling time. Thus the predictive value of UNG for pemetrexed response extends beyond the association of UNG with replication.

Fluctuations in UNG expression significantly impact pemetrexed sensitivity, consistent with the prior observation that glycosylase activity is a major rate-determining step of BER. Recently, we reported that $UNG^{-/-}$ DLD1 cells accumulated uracil and were hypersensitive to pemetrexed. Here, through siRNA and shRNA knockdown of UNG we demonstrate the consistency of this phenotype in lung cancer cell lines, a clinically relevant model system. Decreased AP site formation in pemetrexed-treated UNG knockdown lung cancer cells suggests reduced uracil removal. Previous publications have suggested that substituting uracil for thymine reduces background DNA methylation, alters DNA structure and interferes with high-affinity protein-DNA interactions. Heavily uracilated DNA may therefore impede access and/or activity of transcription factors and replication fork proteins. In our study, we have observed compromised replication fork stability in the absence of uracil excision by UNG. Sensitivity to pemetrexed in UNG deficient cells is rescued by supplemental thymidine, which attenuates UNG induction response and AP site formation in parental cells. Based on these data, we propose a novel hypothesis for thymineless death in UNG deficient cells wherein lack of repair of misincorporated uracil leads to the collapse of DNA replication forks and triggers apoptosis.

That unrepaired uracil-DNA elicits a profound cytotoxic response in pemetrexed-treated human cancer cells was unexpected given the normal development of young $UNG^{-/-}$ mice and comparable sensitivity of $UNG^{+/+}$ and $UNG^{-/-}$ MEFs to fluoropyrimidine TYMS inhibition. Our data are consistent with earlier reports of a direct role for uracil misincorporation in pemetrexed cytotoxicity. Indeed, RNA interference-mediated silencing of dUTPase, an enzyme responsible for maintaining low dUTP levels, significantly enhances pemetrexed cytotoxicity presumably due to increased dUTP incorporation. At baseline, otherwise isogenic UNG-proficient and -deficient cells have comparable levels of DNA damage markers despite reduced capacity for uracil excision suggesting UNG loss is well tolerated in the absence of TS-inhibitor challenge. When exposed to pemetrexed, however, $UNG^{-/-}$ human cancer cells accumulate up to 40-fold more uracil compared to $UNG^{+/+}$ controls. In contrast, only 1.5-fold and 8-fold increases in uracil were reported in 5-FU and FdUrd treated $UNG^{-/-}$ MEFs and raltitrexed treated 293t cells expressing the bacteriophage UNG inhibitor Ugi, respectively. These studies concluded that UNG activity did not impact TYMS sensitivity. We believe the differential sensitivity to various TYMS inhibitors with UNG loss points to an as yet undetermined threshold of genomic uracil tolerance in mammalian cells. Such a threshold has been suggested and is presumed to depend upon both the TYMS inhibitor used and the uracil excision capacity of the cells studied. We speculate previous observations of little correlation of UNG with TYMS sensitivity are due to uracil accumulation within tolerance levels in those model systems.

A clear advantage to the identification of UNG as a predictive marker for pemetrexed resistance is the ability to potentiate pemetrexed efficacy via BER inhibition. We show that UNG is induced by acute and chronic pemetrexed exposure in lung cancer cell lines and MX inhibition of BER restores pemetrexed sensitivity in chronically exposed cells. MX-bound AP sites are clastogenic, trapping TopoIIα in a cleavable complex resulting in DNA DSBs. Cells with high TopoIIα expression are particularly sensitive to DNA damaging agents when combined with MX. Like UNG, TopoIIα levels are elevated in human lung cancer and are highest in small and squamous cell carcinoma. Therefore, the pemetrexed/MX combination is a rational strategy to overcome pemetrexed insensitivity in certain lung cancer subtypes and to restore sensitivity in cells that acquire resistance due to chronic pemetrexed exposure.

Pemetrexed/MX combination therapy has been pursued in phase I clinical trials involving solid tumors resulting in a partial response in 56% of patients enrolled. Among the responders were 3 patients with squamous cell lung carcinoma and 1 patient with squamous oropharyngeal carcinoma that notably had high TYMS levels. Based on these data, phase 2 and randomized controlled trials involving pemetrexed and methoxyamine are planned.

Tailoring chemotherapy based on histological subtype and biomarker expression is a favorable strategy for aggressive, treatment-refractory malignancies such as lung cancer. Our observations that UNG expression is elevated in experimental models of pemetrexed-resistant lung cancer and correlates with pemetrexed efficacy prompt us to propose UNG as a novel predictive marker for pemetrexed in human lung cancer. Moreover, because UNG loss and BER inhibition with MX potently restore pemetrexed sensitivity in resistant cells, UNG-directed BER may be a novel therapeutic target, distinct from the folate metabolism pathway, for overcoming pemetrexed resistance in human lung cancer.

Other embodiments of the invention will be apparent to those skilled in the art from a consideration of the specification or practice of the invention disclosed herein. It is intended that the specification and examples be considered as exemplary only, with the true scope of the invention being indicated by the following claims. All patents, publication, and referenced cited are incorporated by reference in their entirety.

Having described the invention, the following is claimed:

1. A method of determining the susceptibility of human non-small cell lung cancer in a subject to treatment with pemetrexed that induces or promotes incorporation of a UDG substrate into DNA of cancer cells, comprising:
   obtaining a sample of cancer cells from the subject;
   measuring the level of UDG in the cancer cells;
   comparing the measured levels of UDG in the cancer cells to a control level; wherein an increase in the measured levels of UDG in the cancer cells compared to a control level indicates that the cancer is less susceptible to treatment with pemetrexed;
   treating the cancer in the subject with pemetrexed and methoxyamine if the measured level of UDG activity is increased relative to the control level.

2. The method of claim 1, wherein the pemetrexed promotes introduction of uracil or a UDG substrate into the cancer cell DNA.

3. A method of treating human non-small cell lung cancer in a subject comprising:
   obtaining a sample of cancer cells from the subject;
   measuring the level of UDG expression in the cancer cells;
   comparing the measured levels of UDG expression in the cancer cells to a control level; and
   administering pemetrexed that induces or promotes incorporation of a UDG substrate into DNA of cancer cells to the subject if the measured level of UDG expression is decreased compared to a control level or administering pemetrexed in combination with an AP endonuclease inhibitor if the measured level of UDG expression is increased compared to a control level.

4. The method of claim 3, wherein the AP endonuclease inhibitor is administered at an amount effective to potentiate the cytotoxicity of pemetrexed administered to the cancer cells.

5. The method of claim 3, wherein the AP endonuclease inhibitor is selected from group consisting of methoxyamine, O-benzylohydroxylamine; ethyl aminooxyacetate; aminooxyacetic acid; ethyl aminooxyacetate; $H_2NOCHMeCO_2H$; carboxymethoxyamine; aminooxyacetic acid; $HN=C(NH_2)SCH_2CH_2ONH_2$; $H_2NO(CH_2)_3SC(NH_2)=NH$; $MeOC(O)CH(NH_2)CH_2ONH_2$; $H_2NOCH_2CH(NH_2)CO_2H$; canaline; $H_2NO(CH_2)_4ONH_2$; O-(p-nitrobenzyl)hydroxylamine; 2-amino-4-(aminooxymethyl)thiazole; 4-(aminooxymethyl)thiazole; O,O'-(o-phenylenedimethylene)dihydroxylamine; 2,4-dinitrophenoxyamine; O,O'-(m-phenylenedimethylene)dihydroxylamine; O,O'-(p-phenylenedimethylene)dihydroxylamine; $H_2C=CHCH_2O-NH_2$; $H_2NO(CH_2)_4ONH_2$; $H_3C-(CH_2)_{15}-O-NH_2$, 2,2'-(1,2-ethanediyl)bis(3-aminooxy)butenedioic acid dimethyl diethyl ester;

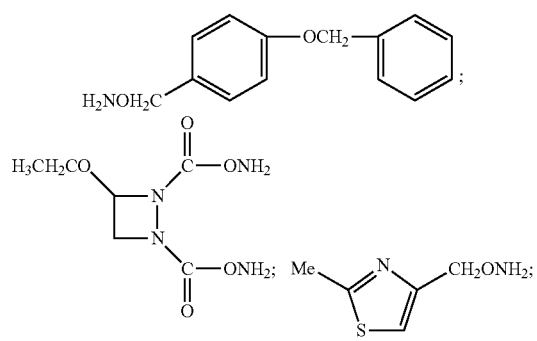

-continued

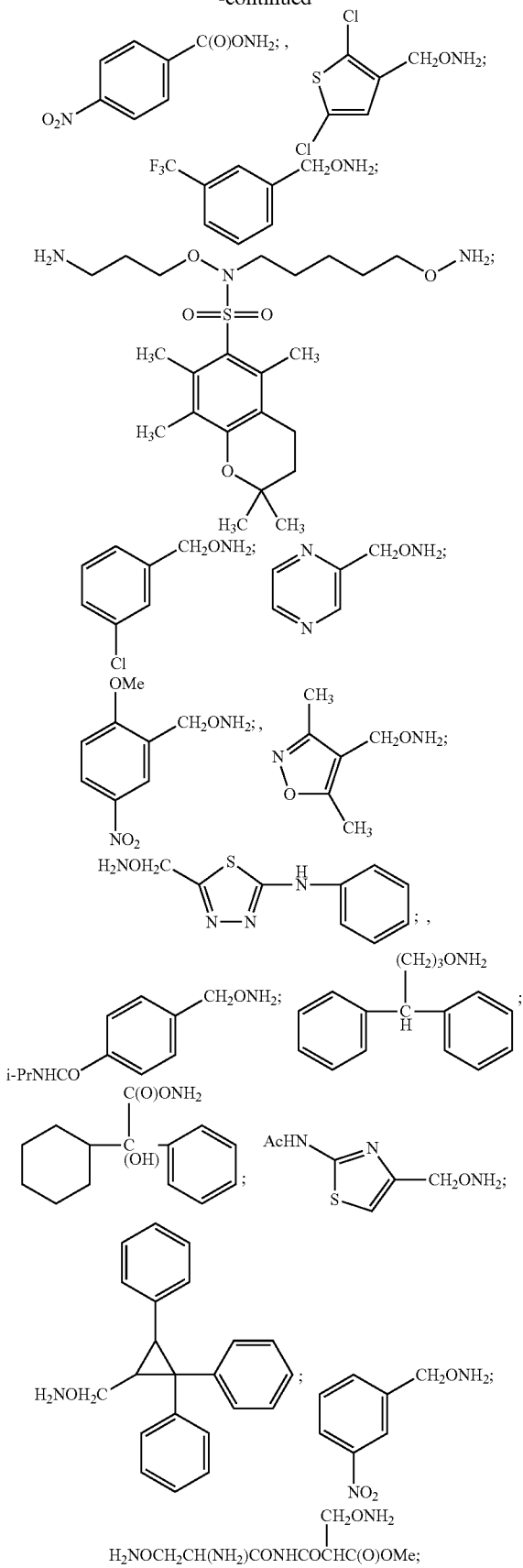
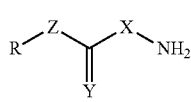
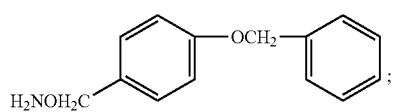

a compound having a structure of Formula I:

Formula I wherein X is O or NH,

Y is O, S, or NH,

Z is absent or represents O, S, or NH, and

R represents a hydrogen or a hydrocarbon moiety, and pharmaceutically acceptable salts thereof.

6. The method of claim 3, the AP endonuclease inhibitor comprising methoxyamine.

7. The method of claim 6, wherein the amount of methoxyamine is an amount sufficient to sensitize the cancer cells to the pemetrexed without causing undue sensitization of normal cells.

8. A method of treating a pemetrexed-resistant cancer in a subject comprising:

obtaining a sample of cancer cells that have been exposed to pemetrexed from the subject;

measuring the level of UDG in the cancer cells;

comparing the measured levels of UDG in the cancer cells to a control level; wherein an increase in the measured levels of UDG in the cancer cells compared to a control level indicates that the cancer is less susceptible to treatment with pemetrexed; and administering pemetrexed in combination with an AP endonuclease inhibitor if the measured level of UDG expression is increased compared to a control level.

9. The method of claim 8, wherein the pemetrexed promotes introduction of uracil or a UDG substrate into the cancer cell DNA.

10. The method of claim 8, wherein the AP endonuclease inhibitor is administered at an amount effective to potentiate the cytotoxicity of pemetrexed administered to the cancer cells.

11. The method of claim 8, wherein the AP endonuclease inhibitor is selected from group consisting of methoxyamine, O-benzylohydroxylamine; ethyl aminooxyacetate; aminooxyacetic acid; ethyl aminooxyacetate; $H_2NOCHMeCO_2H$; carboxymethoxyamine; aminooxyacetic acid; $HN=C(NH_2)SCH_2CH_2ONH_2$; $H_2NO(CH_2)_3SC(NH_2)=NH$; $MeOC(O)CH(NH_2)CH_2ONH_2$; $H_2NO-CH_2CH(NH_2)CO_2H$; canaline; $H_2NO(CH_2)_4ONH_2$; O-(p-nitrobenzyl)hydroxylamine; 2-amino-4-(aminooxymethyl)thiazole; 4-(aminooxymethyl)thiazole; O,O'-(o-phenylenedimethylene)dihydroxylamine; 2,4-dinitrophenoxyamine; O,O'-(m-phenylenedimethylene)dihydroxylamine; O,O'-(p-phenylenedimethylene)dihydroxylamine; $H_2C=CHCH_2ONH_2$; $H_2NO(CH_2)_4ONH_2$; $H_3C-(CH_2)_{15}-O-NH_2$, 2,2'-(1,2-ethanediyl)bis(3-aminooxy)butenedioic acid dimethyl diethyl ester;

-continued

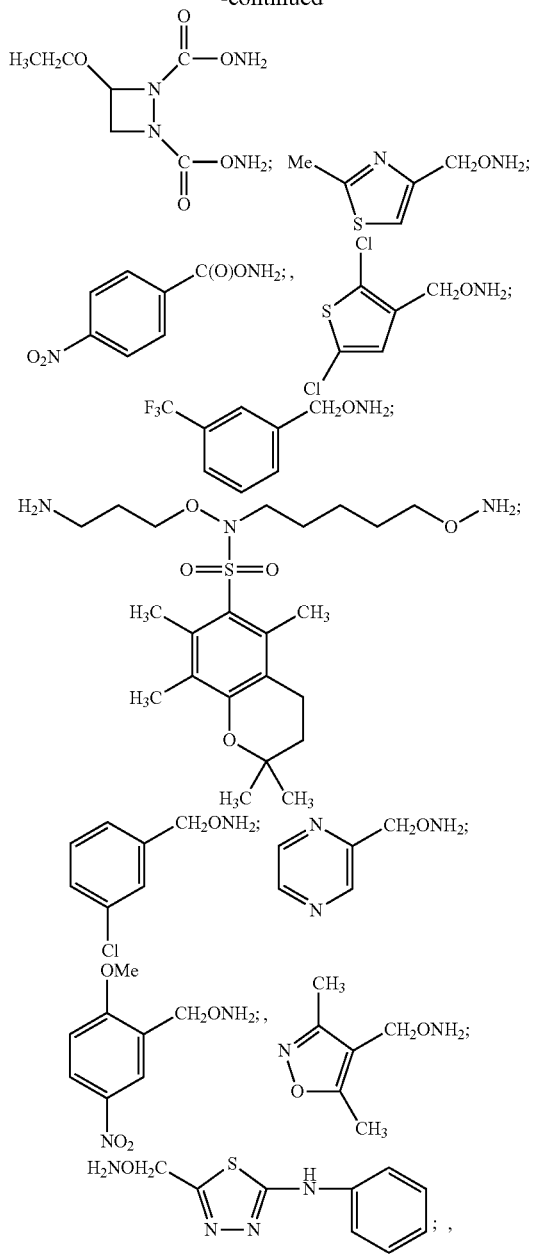

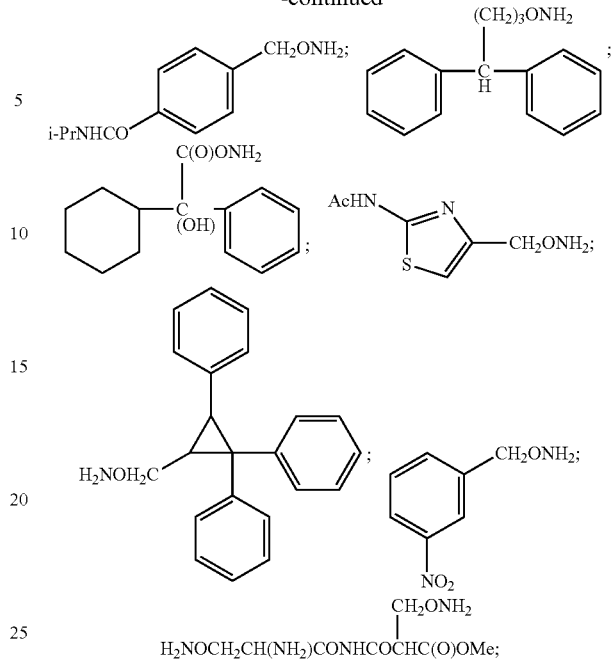

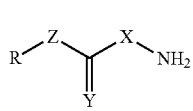

$H_2NOCH_2CH(NH_2)CONHCOCHC(O)OMe$;

a compound having a structure of Formula I:

$$R-Z-\underset{Y}{\overset{X}{C}}-NH_2 \qquad \text{Formula I}$$

wherein X is O or NH,
Y is O, S, or NH,
Z is absent or represents O, S, or NH, and
R represents a hydrogen or a hydrocarbon moiety,
and pharmaceutically acceptable salts thereof.

12. The method of claim 8, the AP endonuclease inhibitor comprising methoxyamine.

13. The method of claim 12, wherein the amount of methoxyamine is an amount sufficient to sensitize the cancer cells to the pemetrexed without causing undue sensitization of normal cells.

* * * * *

SEQUENCE LISTING

<160> NUMBER OF SEQ ID NOS: 2

<210> SEQ ID NO 1
<211> LENGTH: 40
<212> TYPE: DNA
<213> ORGANISM: Homo sapiens

<400> SEQUENCE: 1
gtaaaacgac ggccagtgua ttcgagctcg gtacccgggg         40

<210> SEQ ID NO 2
<211> LENGTH: 40
<212> TYPE: DNA
<213> ORGANISM: Homo sapiens

<400> SEQUENCE: 2
cattttgctg ccggtcacgg aagctcgagc catgggcccc         40